(12) United States Patent
Ananian et al.

(10) Patent No.: US 8,645,865 B2
(45) Date of Patent: Feb. 4, 2014

(54) SYSTEMS AND METHODS FOR SPECIFYING AN ITEM ORDER

(75) Inventors: John Allen Ananian, Winchester, CA (US); James D. Bryan, Ladera Ranch, CA (US)

(73) Assignee: Direct Response Medicine, LLC, Winchester, CA (US)

( * ) Notice: Subject to any disclaimer, the term of this patent is extended or adjusted under 35 U.S.C. 154(b) by 627 days.

(21) Appl. No.: 12/604,336

(22) Filed: Oct. 22, 2009

(65) Prior Publication Data

US 2010/0100848 A1 Apr. 22, 2010

Related U.S. Application Data

(60) Provisional application No. 61/107,577, filed on Oct. 22, 2008.

(51) Int. Cl.
*G06F 3/048* (2013.01)

(52) U.S. Cl.
USPC ........... 715/834; 715/708; 715/759; 715/841; 715/853; 715/866

(58) Field of Classification Search
None
See application file for complete search history.

(56) References Cited

U.S. PATENT DOCUMENTS

| 6,920,445 | B2 * | 7/2005 | Bae ........................................ 1/1 |
| 7,174,516 | B2 * | 2/2007 | Chipchase .................... 715/763 |
| 2002/0191030 | A1 | 12/2002 | Trajkovic et al. |
| 2004/0143512 | A1 * | 7/2004 | Sturr, Jr. ......................... 705/26 |
| 2004/0153504 | A1 * | 8/2004 | Hutchinson et al. .......... 709/204 |
| 2006/0069603 | A1 * | 3/2006 | Williams et al. ................... 705/9 |
| 2006/0173754 | A1 | 8/2006 | Burton et al. |
| 2006/0259373 | A1 * | 11/2006 | Perrier et al. .................... 705/26 |
| 2008/0040671 | A1 * | 2/2008 | Reed ............................. 715/738 |
| 2009/0132963 | A1 * | 5/2009 | Morita et al. ................. 715/834 |

OTHER PUBLICATIONS

ISA United States, International Search Report of PCT/US09/61734, Dec. 10, 2009, WIPO, 3 pages.

* cited by examiner

*Primary Examiner* — Doon Chow
*Assistant Examiner* — Anil N Kumar
(74) *Attorney, Agent, or Firm* — Alleman Hall McCoy Russell & Tuttle LLP

(57) ABSTRACT

An embodiment of a graphical user interface for specifying an item order includes a graphical order generator arranged in a geometric pattern. The graphical order generator may include an order input tool including a category section for displaying a plurality of inter-dependent dynamically filtered category indicators arranged in a sequential and user-modifiable hierarchy, and an option section for displaying a plurality of selectable option indicators associated with a category indicator. The category indicator may include a graphical representation of an active state or incomplete state before selection of an option indicator, and a graphical representation of a complete state after selection of the option indicator. The graphical order generator may also include a communication tool for displaying a plurality of selectable communication indicators associated with one or more past or current communication messages, and a contextual information tool for displaying one or more selectable information indicators.

19 Claims, 13 Drawing Sheets

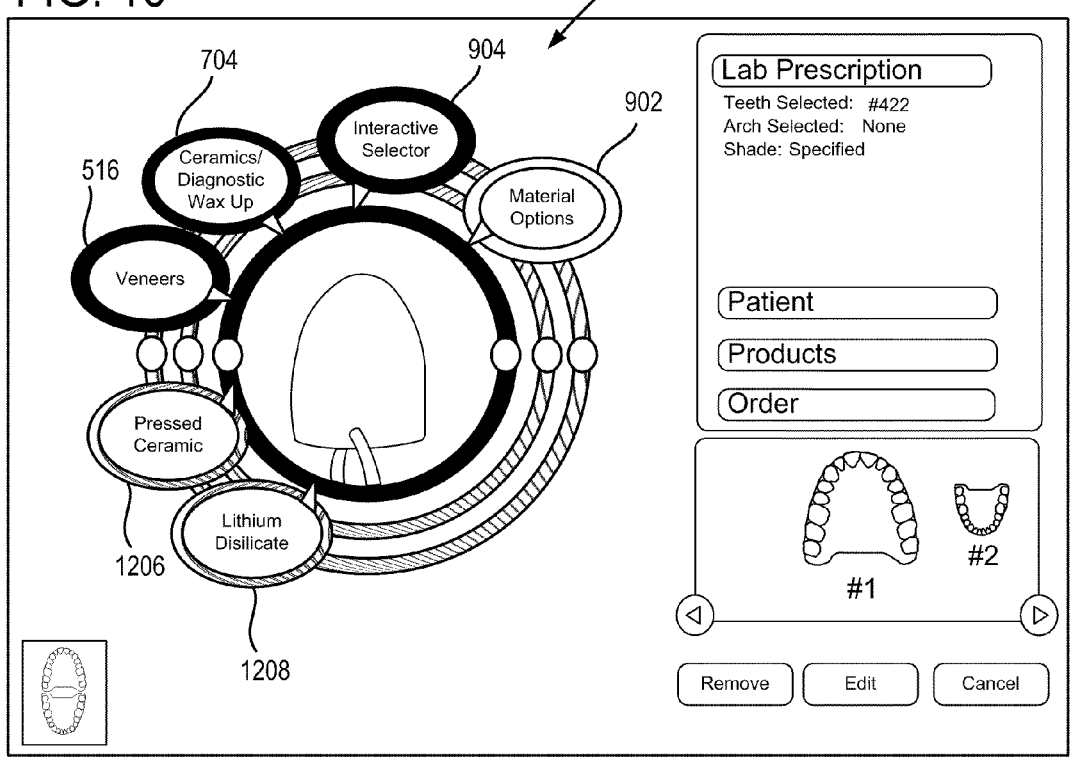

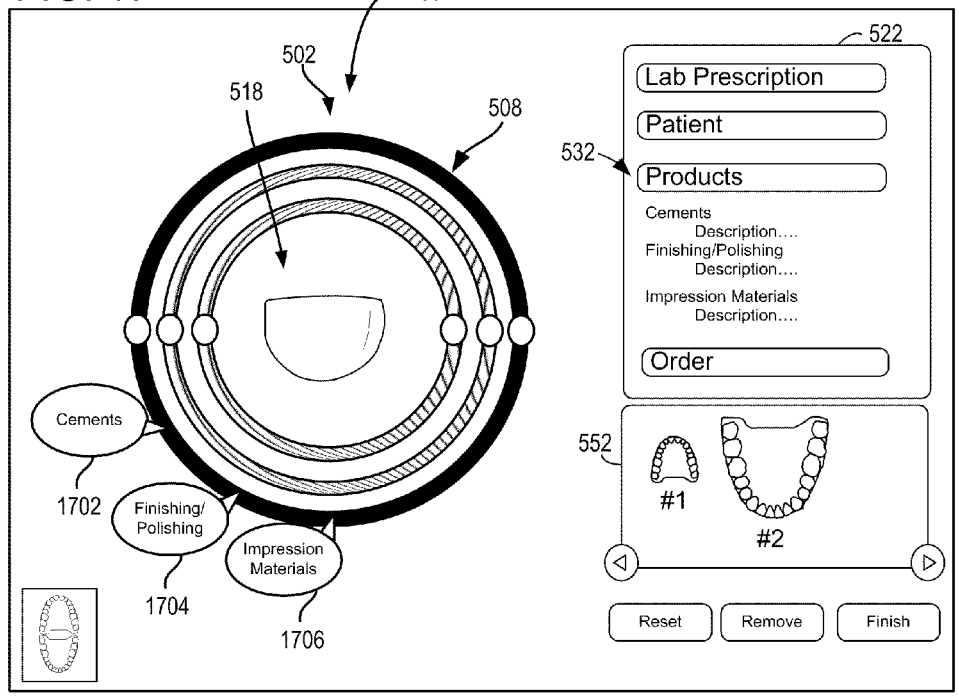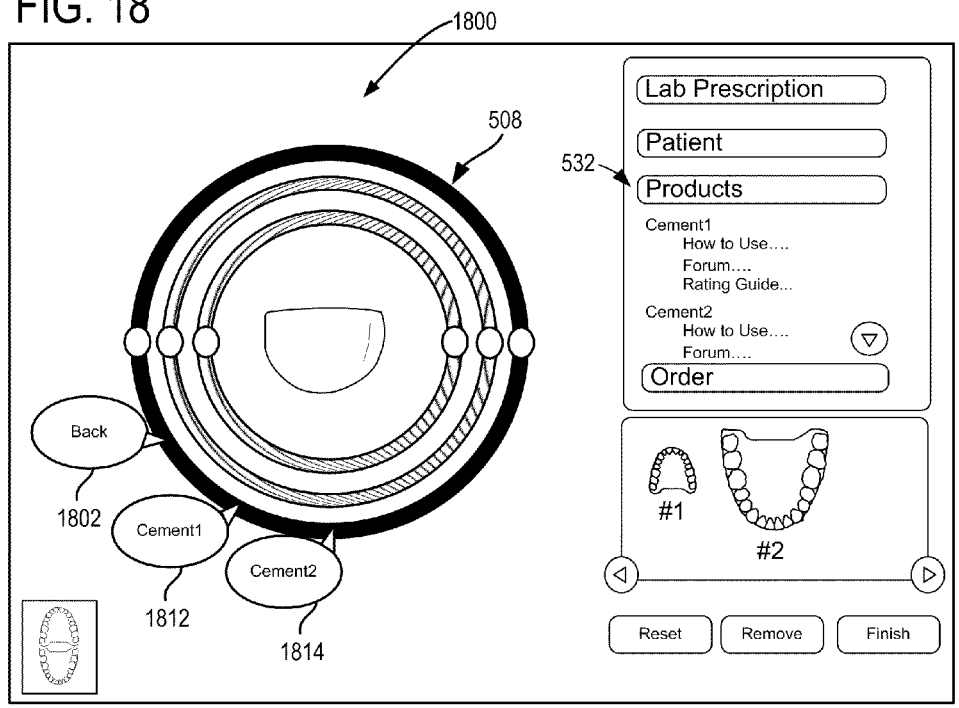

SYSTEMS AND METHODS FOR SPECIFYING AN ITEM ORDER

CROSS REFERENCE TO RELATED APPLICATION

This application claims priority to U.S. Provisional Application No. 61/107,577, filed Oct. 22, 2008, and titled COMPUTING DEVICE FOR DISPLAYING A GRAPHICAL USER INTERFACE FOR A HEALTHCARE ORDERING APPLICATION. The entirety of the above listed application is incorporated herein by reference for all purposes.

BACKGROUND

When a client is ordering a custom-made item, there are typically multiple parameters to be specified. Further, the parameters may have a wide variety of interrelationships, where choosing one parameter can restrict or broaden other parameter options. For example, different manufacturers may offer different models of an item. Thus, if a client is presented with a list of manufacturers of a product and the client chooses a particular manufacturer, the client may also select a particular parameter for the item that the selected manufacturer cannot provide. Thus, current systems for generating product or service orders can lead to incomplete specification of an order, miscommunication between client and provider, and incompatible parameters being selected, among other problems. This presents a challenge for organizing information in a system for generating item orders.

SUMMARY

Systems and methods for specifying an item order are provided herein. One exemplary system includes a graphical user interface of an application which facilitates organization and communication of multichannel information. One embodiment of such a graphical user interface includes an item selection screen configured to display a selectable item. The graphical user interface may also include a graphical order generator arranged in a geometric pattern, displayable in response to selection of the selectable item.

The graphical order generator may include an order input tool, a communication tool, and a contextual information tool. The order input tool may include a category section configured to display a plurality of inter-dependent dynamically filtered category indicators arranged in a sequential and user-modifiable hierarchy, and an option section configured to display a plurality of selectable option indicators associated with a category indicator. The category indicator may include a graphical representation of an active state or incomplete state prior to selection of an option indicator, and a graphical representation of a complete state after selection of the option indicator.

The communication tool may be configured to display a plurality of selectable communication indicators associated with one or more past or current communication messages. The contextual information tool may be configured to display one or more selectable information indicators which are dynamically updateable in response to a change of state of the category indicator and in response to a change of selectable option indicators.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

BRIEF DESCRIPTION OF THE DRAWINGS

FIG. 16 illustrates a schematic view of another screen of the first embodiment of the graphical user interface of FIG. 4.

FIG. 17 illustrates a schematic view of a screen of a second embodiment of a graphical user interface including a graphical order generator.

FIG. 18 illustrates a schematic view of another screen of the second embodiment of the graphical user interface of FIG. 17.

DETAILED DESCRIPTION

Figure 1:
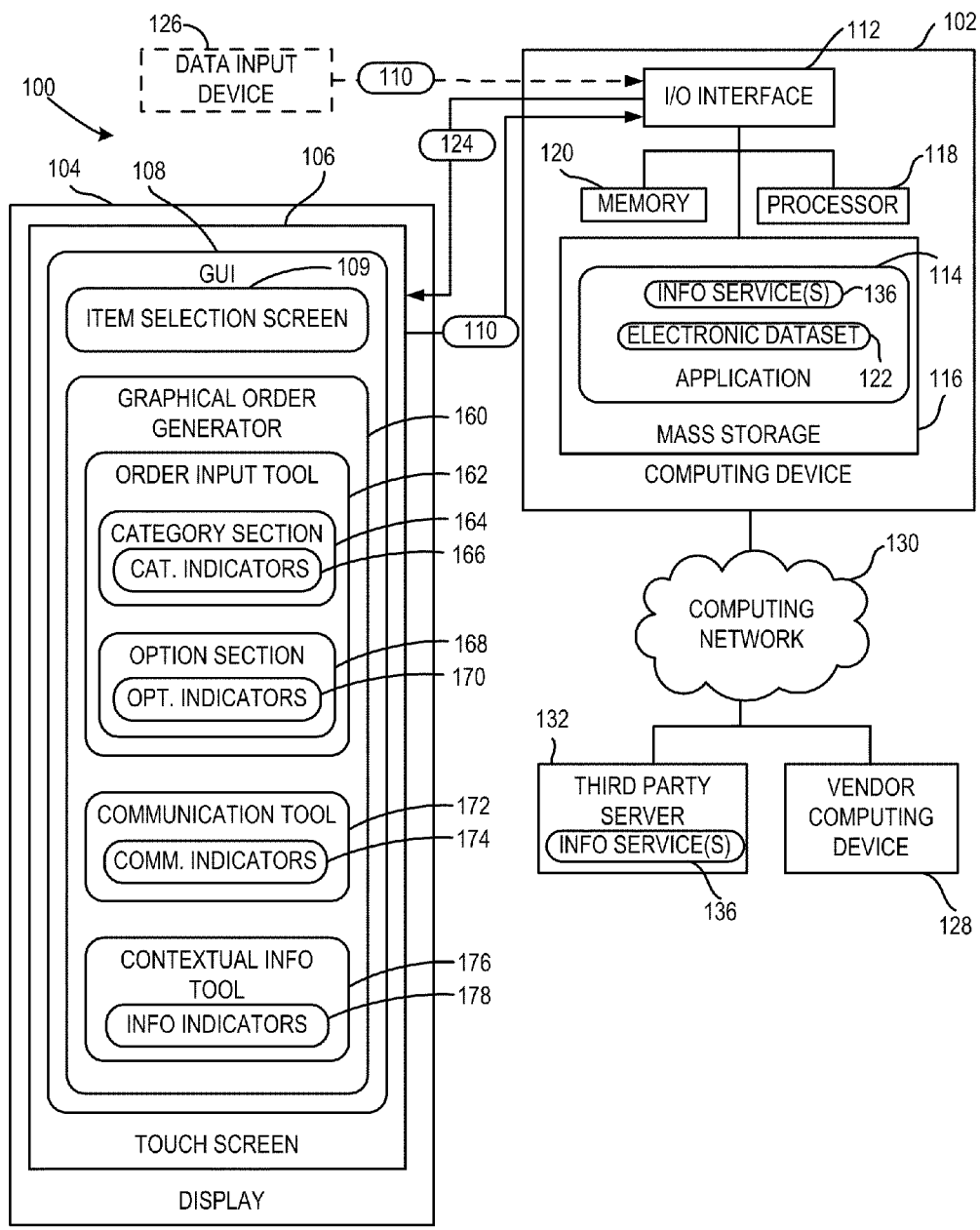
FIG. 1 shows a schematic view of an embodiment of a system including a computing device configured to display a graphical user interface for an ordering application.
Figure 2:
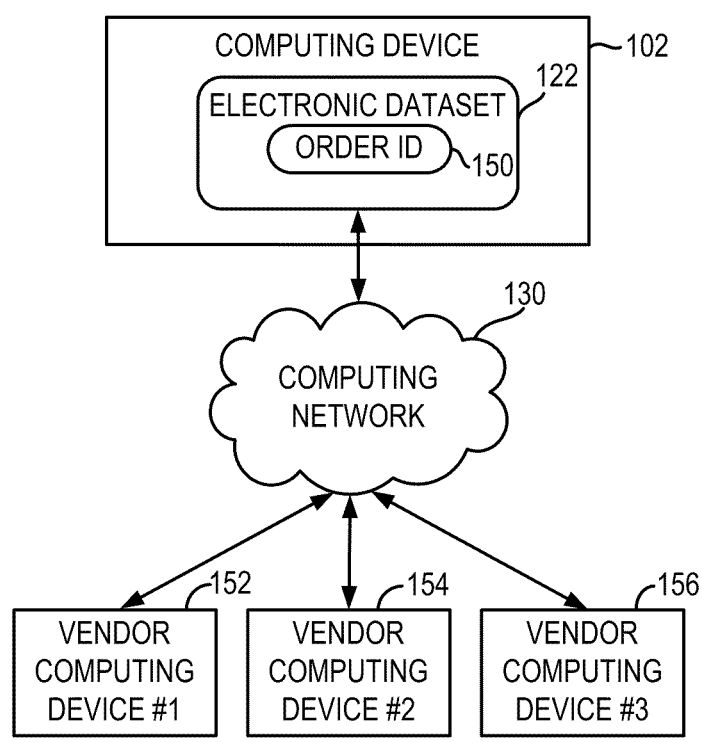
FIG. 2 shows a schematic view of input and output of an electronic dataset associated with an order.
Figure 3:
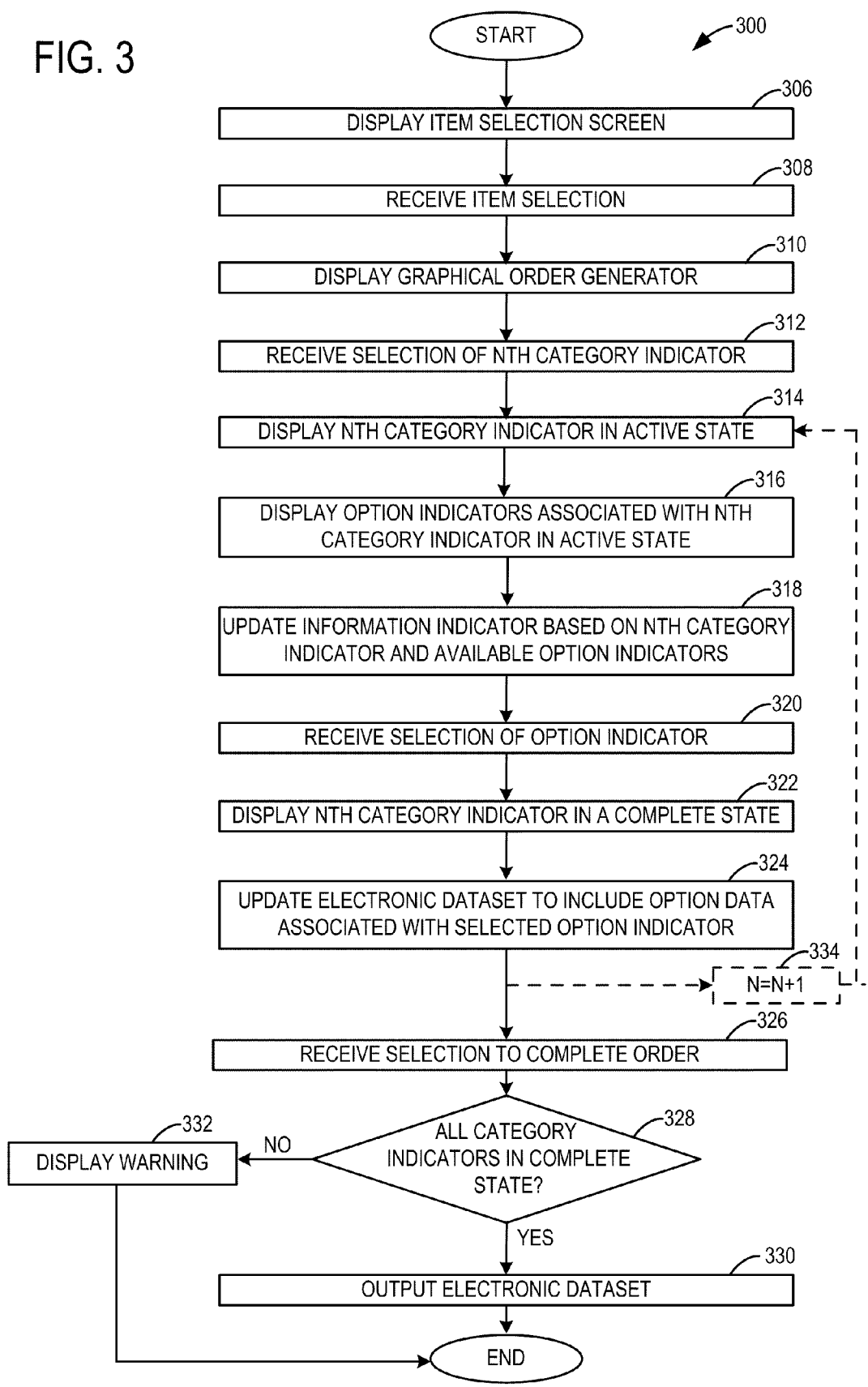
FIG. 3 is a flowchart illustrating a method for specifying an order.

Current systems for generating item orders (e.g., for a product or service) can lead to incomplete specification of a product or service, miscommunication between a client and a provider, and incompatible parameters being selected, among other problems. FIG. 1 illustrates an exemplary system to address this problem, which includes a computing device for displaying a graphical user interface (GUI) that guides a user when specifying an order for an item or service. FIG. 2 illustrates a schematic arrangement for receiving input regarding an electronic dataset corresponding to an item order and for outputting the electronic dataset. Thereafter, FIG. 3 illustrates a method for using a system such as that presented in FIGS. 1-2.

An exemplary series of screens showing usage of a graphical user interface (GUI) of the system of FIGS. 1-2 are illustrated and described with respect to FIGS. 4-16. Additional embodiments of suitable GUIs of the system are illustrated and described with respect to FIGS. 17-20. As will be appreciated, the systems and methods provided herein may allow for accurate and complete item order specification, and an enjoyable and satisfying user experience.

Referring now to FIG. 1, a schematic view of an embodiment of a system 100 including a computing device 102 configured to execute an ordering application 114 is shown. Application 114 is configured to display a graphical user interface (GUI) 108 on an associated display 104, and receive input data 110 via touch screen 106 in this example. In other examples, input data 110 may be received at the computing device 102 from a data input device 126, such as a keyboard, mouse, or other peripheral or remote device. The input data 110 may indicate selections regarding ordering or specifying an item, as discussed below.

The GUI 108 may be used to specify characteristics of a custom-made item. Upon initiation of display of GUI 108 (e.g., initiation of an order), a corresponding electronic dataset 122 may be created and stored at least temporarily at the computing device 102. Thereafter, as specifications are made to the order via the GUI 108, updates may be sent to the computing device to update the electronic dataset 122.

The GUI 108 may include an item selection screen 109 configured to display a selectable item within an environmental or use context. For example, one or more teeth may be selected from a mouth graphic, thus providing a context from which to select the teeth. In another example, one or more body parts may be selected from a schematic body graphic. Further still, one or more of a plurality of car models may be selected.

The GUI may also include a graphical order generator 160 arranged in a geometric pattern. In some cases, the graphical order generator 160 is displayable in response to selection of a selectable item. The graphical order generator 160 itself may include an order input tool 162 with a category section 164 configured to display a plurality of inter-dependent dynamically filtered category indicators 166 arranged in a sequential and user-modifiable hierarchy. The graphical order generator 160 may also include an option section 168 configured to display a plurality of selectable option indicators 170 associated with a particular category indicator in response to selection of the category indicator.

As will be discussed and illustrated in detail with respect to FIGS. 4-16, before an option indicator is selected for a corresponding category indicator, the corresponding category indicator may include a graphical representation of an active state or an incomplete state. After selection of an option indicator, the corresponding category indicator may include a graphical representation of a complete state, and the electronic dataset 122 may be accordingly updated to include an option associated with the selected option indicator.

Similarly, option indicators may include a graphical representation of an active state, incomplete state, or complete state. For example, an option indicator may be in an active state when the user has placed a cursor over the option indicator, or if the user has tentatively selected the option indicator. The option indicator may be in an incomplete state if it is unselected. Further, the option indicator may be in a complete state if the option indicator has been selected for a particular category.

As shown in FIG. 1, the graphical order generator 160 may also include a communication tool 172 configured to display a plurality of selectable communication indicators 174. The communication indicators 174 may be associated with one or more past or current communication messages, such as annotations by a user, or communications between a client and vendor. The communication tool 172 may enable voice messaging, VOIP, text messaging, video chat, etc. Accordingly, the electronic dataset 122 may include communication data associated with the one or more past or current communication messages.

The graphical order generator 160 may also include a contextual information tool 176 configured to display one or more selectable information indicators 178. The information indicators 178 may provide links to information services 136, such as an informational file. In some cases, an information service may include an information sub-application (not shown). Information services 136 may be internal to the application 114 and/or may be located remotely, such as on a third party server 132. The information indicators 178, as displayed on the GUI 108, may be dynamically updated based on selection of a category indicator and/or selection of an option indicator. In this way, the information indicators 178 and corresponding information services 136 may be relevant to the user at any given moment. Furthermore, the information indicators may be updated based on a state of category indicators and/or the population of option indicators available for selection.

Input data 110 may be relayed via an I/O interface 112, to application 114 (e.g., an ordering application) located in a mass storage 116 of the computing device 102. Relay of data involves a processor 118 and portions of memory 120. Within the application 114, the electronic dataset 122 associated with the order is updated by the input data 110. Examples of input data 110 may include selection of any portion of the GUI 108 for focus, selection of an option for an item order, an update to the electronic dataset, etc. As in the depicted embodiment, the application 114 can update output data 124 to the display 104 via an I/O interface 112, in order to update the GUI based on input data 110 received at the computing device 102, for example.

As will be discussed later with respect to communicating with a vendor, the computing device 102 can be connected to a vendor computing device 128 via a computer network 130. The computing device 102 may also communicate with a third party server 132 via computer network 130. In one example, application 114 may receive an information service from a third party server or vendor computing device (e.g., download a media file from third party server 132 or vendor computing device 128) and integrate the information service into the GUI 108 of the application 114, such that the information service can be executed by computing device 102 even if computing device 102 is later disconnected from computer network 130. Further, the computing device may send the electronic dataset 122 to vendor computing device 128 to request fulfillment of the order as specified.

Referring now to FIG. 2, a schematic view of the electronic dataset 122 incoming and outgoing from the computing device 102 is shown. The electronic dataset may include an order identification 150, among other parameters such as patient information, communication history, and contextual information, described herein. The electronic dataset 122 may be sent from the computing device 102 through the computer network 130 and then to one or more vendor computing devices. Depicted in this example are vendor computing device #1 152, vendor computing device #2 154, and vendor computing device #3 156, though any number of vendor computing devices or third party computing devices is conceivable. Further, the vendor computing devices 152, 154, and 156 can be configured to perform actions or functions on the electronic dataset 122 via the computer network 130.

The electronic dataset 122 may be output from the computing device upon completion of a custom-made item order, and/or updates to the electronic dataset may be output from the computing device along with the order identification, to thereby reduce an amount of data being transmitted.

It may be appreciated that the electronic dataset 122 can be divided into multiple parts to be sent to multiple vendors and/or service providers to enhance workflow management in some examples. For example, where an electronic dataset 122 includes more than one prescription, each prescription may be sent to a different vendor computing device. However, they may be linked by the order identification 150 as each electronic dataset may be assigned, in part or in whole, an order identification 150 by which data and physical assets can be linked. One example of an order identification 150 may be a barcode, which may be used as described below.

Turning now to FIG. 3, an exemplary method 300 for ordering an item, including specifying an electronic dataset, is provided. At 306, the method 300 includes displaying an item selection screen including a selectable item. For example, if an application is a healthcare order application, the selectable items may include body parts, by which a medical problem can be specified. In another example, if the application is an automobile item order application, the selectable items may include automobile models or parts, or locations on or within an automobile. Further still, if the application is a legal services ordering application, the selectable items may be types of legal services, or geographical regions. At 308, the method 300 may include receiving a selection of the selectable item, for example, via user input.

At 310, the method 300 includes displaying a graphical order generator of a GUI on a display. This may include displaying an order input tool configured to display a plurality of interdependent dynamically-filtered category indicators arranged in a sequential and user-modifiable hierarchy, a communication tool, and/or an information tool configured to display a plurality of information indicators. In one example, a first one of the category indicators is displayed with a graphical representation of an incomplete state, and the category indicator is at least partially overlaid on the geometric arrangement of the order generator tool.

At 312, the method 300 may include receiving a selection of a category indicator, such as the first one (n=1) of the category indicators. In response, the method 300 may include displaying the first one of the category indicators with a graphical representation of an active state at 314, and displaying a plurality of selectable option indicators associated with the first one of the category indicators at 316. Further, at 318, the method 300 may include updating the information indicators based on the active state of the first one of the category indicators and based on the plurality of selectable option indicators. That is, the information indicators may be changed to reflect information that is relevant to the category being displayed and/or relevant to the options being displayed.

At 320, the method 300 further includes receiving a selection of one of the selectable option indicators. In response, the method 300 may include displaying the first one of the category indicators with a graphical representation of a complete state at 322. Furthermore, an electronic dataset may be updated at 324 to include option data associated with a selected option indicator.

In some examples, and as discussed later in detail, the method 300 may also include proceeding to 334 where a counter is incrementally increased, and thereafter returning to 314, where a next category indicator is displayed in the active state. That is, the method 300 may include displaying a second category indicator with a graphical representation of an incomplete state or an active state in response to receiving selection of a selectable option indicator. In such a case, the second category indicator may be lower in the category indicator hierarchy than the first category indicator. Where two or more category indicators (e.g., a first category indicator and a second category indicator) are displayed, the method 300 may also include moving a second one of the category indicators higher in the hierarchy than the first one of the category indicators, responsive to user input. In response to said moving, the method 300 may include updating the plurality of selectable option indicators associated with the first category indicator based on the moving of the second category indicator.

However, the method 300 may include receiving a selection or request to complete an order (e.g., to send the order to a vendor) at 326. Thereafter, the method 300 proceeds to 328 where it is determined if the order is sufficiently completely specified. For example, this may include determining, at 328, if all of the category indicators displayed are in a complete state (e.g., option indicators have been selected for each applicable category indicator).

If this answer is yes at 328, the item order is complete, the item order is complete, and the method 300 includes outputting the electronic dataset at 330. However, if the answer is no at 328, the method proceeds to 332, where a warning is displayed to indicate to a user that the order has not been fully specified. In some examples, the user may be presented with an option to save the order for later completion and/or to delete the order.

Throughout the method 300, the communication tool may display a plurality of communication indicators associated with one or more past or current communication messages in response to selection of the communication tool. Similarly, the method 300 may include displaying an information service in response to receiving selection of an information indicator.

A graphical user interface for specifying an item order may have multiple screens such that a user can choose a context for which the user would like to specify an item order. For example, if a user would like to order an item related to dentistry, the user may be presented with an item selection screen 400 illustrated in FIG. 4. To arrive at item selection screen 400, a user may have launched an executable application and/or may have selected the screen 400 via a series of inputs on previous screens of the GUI. FIGS. 4-16 show schematic views of an embodiment of a series of screens of a GUI, some or all of which may be sequentially presented to a user. These screens are designed to assist the user in navigating the complex interrelationships of the product specifications. Thereafter, FIGS. 17-20 illustrate alternative embodiments of the GUI.

Figure 4:
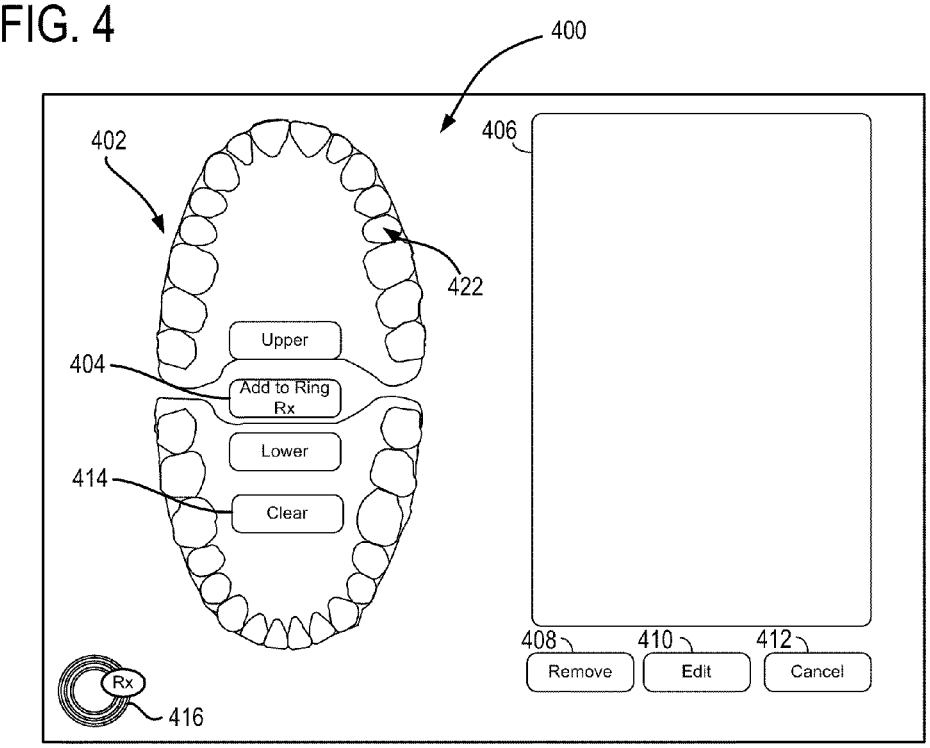
FIG. 4 is a schematic view of a screen of a first embodiment of a graphical user interface for selecting an item for order, of the system of FIG. 1.

Referring now to FIG. 4, the item selection screen 400 includes an item selector graphic 402 (e.g., mouth graphic), by which a user can select, by touch input in this example, one or more teeth or mouth locations for which an item is to be ordered. For example, a user may select a tooth for which a crown is to be ordered, or an upper palette for which a dental guard is to be ordered.

By applying touch input to tooth 422, for example, tooth 422 is tentatively selected. Thereafter, a user may select an add button 404 and tooth 422 may be visually added to selector tray 406. Before actuation of add button 404, selection of a tentatively selected tooth or mouth location can be removed by actuation of clear button 414. However, if tooth 422 is added to selector tray 406 by actuation of add button 404, a graphic of tooth 422 may be shown in selector tray 406. Thereafter, removal of tooth 422 from the selector tray 406 (and thus, from an order specification and electronic dataset) can be executed by user actuation of removal button 408. Although not shown, additional teeth or mouth locations can be added to and/or removed from selector tray 406, and various edit tools for editing the selected teeth and mouth locations can be accessed by actuation of edit button 410. In other words, several prescriptions, or orders can be made via a single beginning-to-end use of the GUI described herein. Further still, an order can be cancelled by actuation of cancel button 412.

If at least one tooth or mouth location, in this example, has been added to the selector tray 406, a user may select prescription icon 416 to proceed to a next screen of the GUI for specifying the item order. That is, a computing device may receive selection of the prescription icon 416, and be configured to display screen 500 of FIG. 5.

Screen 500 includes graphical order generator 502 for guiding the user to sufficiently specify the order using at least order input tool 504. In this way, customized input for a custom-made order of an item may be received As shown on screen 500, the graphical order generator 502 may be arranged in a geometric pattern as a plurality of concentric rings, or nested ring elements. In this example, order input tool 504 is an innermost ring element, a communication tool 506 is a middle ring element, and a contextual information tool 508 is an outermost ring element. The geometric pattern may include one or more circular, oval, or otherwise curved rings, circles, or other shapes. In other examples, the geometric pattern may not be curved, and squares or other polygons or geometric arrangements are employed.

In the example illustrated, the rings (e.g., order input tool 504, communication tool 506, and contextual information tool 508) are divided into hemispheres. For example, a top portion of order input tool 504 is a category section 510 for displaying category indicators, such as category indicator 516. A bottom portion of order input tool 504 is an option section 512 for displaying option indicators. However, in other examples, the geometric pattern or components thereof may be otherwise divided (e.g., into more than two parts), or not divided at all. Some of the components may be incomplete (e.g., a ring may not have a top or bottom portion, etc.)

Each of the tools (e.g., order input tool 504, communication tool 506, contextual information tool 508) may include a scroll function whereby the user can scroll to view all possible links or selectable indicators. For example, a flashing arrow may be provided to indicate a scrolling function on each of the tools, in a "just-in-time" manner. That is, such a flashing arrow may only be provided if scrolling is enabled for the tool.

Further, an order graphic 518 is displayed in a middle of the nested ring elements, for a user's ease of understanding of interrelationships between the tools. Order graphic 518 may be updated as the order is specified (e.g., as category indicators and option indicators are selected) to assist the user in visualizing the custom-made order. The order graphic 518 may include images (e.g., 3-D, rotatable), video, audio, etc. Furthermore, as category indicators and option indicators are selected throughout the order specification process, a corresponding electronic dataset is updated.

Figure 5:
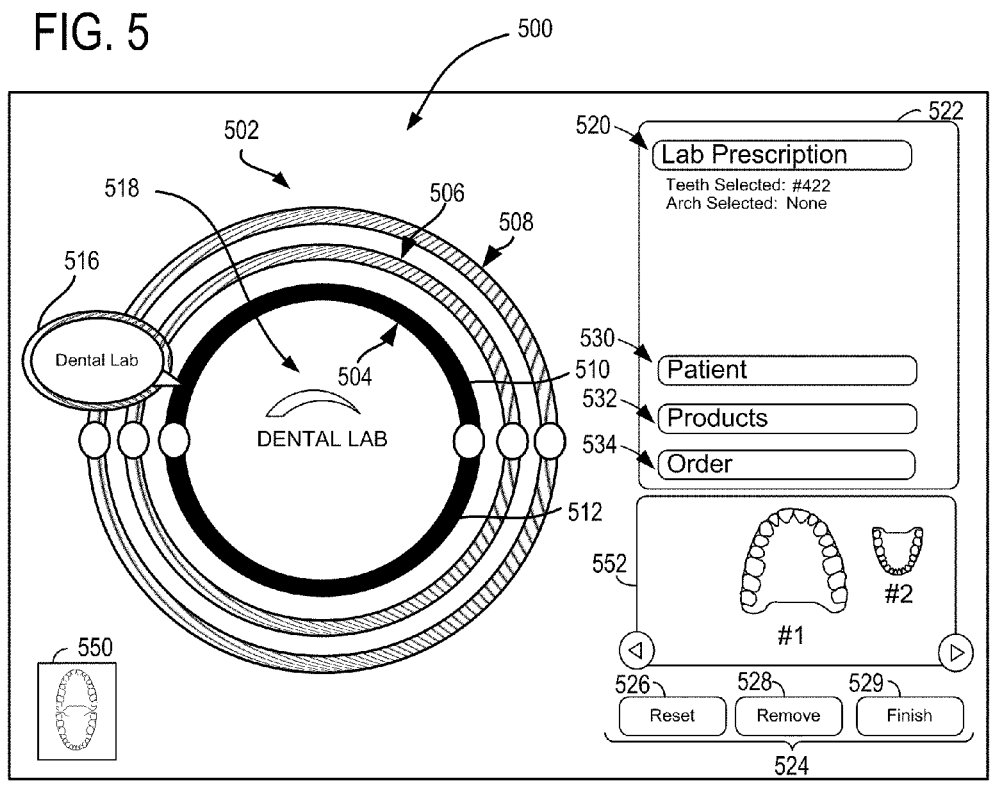
FIG. 5 illustrates a schematic view of another screen of the first embodiment of the graphical user interface of FIG. 4.

As an electronic dataset is updated, text information associated with the electronic dataset may be displayed in a dataset summary pane 520 (e.g., a prescription pane) of an order information window 522 that is displayed throughout the order specification process. For example, the text summary in the dataset summary pane 520 summarizes the item order as an order for a selected tooth #22 at the beginning of the order specification process, as shown in FIG. 5. The dataset summary pane 520 also may include media icons and links to audio and video components, which can be updated as option indicators are selected throughout the order specification process.

The order information window 522 may also include a patient information pane 530, a products pane 532, an order pane 534, an order history pane, and/or an estimate pane, as just some examples. The patient information pane 530 may include information such as patient name, patient age, etc. The products pane 532 may include additional text and/or graphic information about a selected product or related products. The order pane 534 may be configured to contain text information regarding an identification code or status of the order transaction. Furthermore, a history pane may include a patient history or practitioner history. The estimate pane can include a cost or time estimate for the order. These panes may be expandable and collapsible based on user input. An electronic dataset associated with the order may contain one or more of the above types of information.

Throughout the order specification process, if a user is satisfied or dissatisfied with the order specification, the user can make use of the control bar 524 to modify, finish and/or output the order. Specifically, the control bar 524 includes a reset button 526 for clearing details of an order specification, and a remove button 528 for removing a tooth or mouth location (e.g., a prescription, or sub-portion of the order) from the order specification. Actuation of either the reset button 526 or remove button 528 also may update the dataset summary pane 520 and the electronic dataset. Control bar 524 also includes finish button 529, which upon actuation, may send a final electronic dataset to a vendor, for example.

It may be appreciated that control bar 524 illustrates example tools and other controls or navigational tools can be contained in the control bar. In another example, a "call me now" tool may be placed in the control bar 524 to allow a user preparing an order to send a request to be called back by, for example by a lab technician associated with the lab order to discuss the current order in near real-time. The system may be configured to send an order-specific instance of the electronic dataset to the lab technician as part of a "call me now" request, via a data link. The lab technician would be able to view and modify the order on a vendor computing device (e.g., vendor 128), and return any changes to the order as directed by the user for continuity in near real-time. In addition to working with the lab technician in near real-time, it will be appreciated that the order may be passed to the lab technician for asynchronous modification or synchronous dual control modification by the lab technician alone or the lab technician in combination with the user.

Further still, at screen 500, graphic 550 is selectable for navigation to the item selection screen 400, where a user may further modify selected items (e.g., teeth, mouth parts) for order. In another example, upon mouse-over of the tooth selector graphic 550, a magnified pop-up may be presented whereby the user may select a tooth, and the selected tooth may thereafter become the focus of the graphical order generator 502.

Further, throughout the ordering process, there may be one or more navigational tools, for navigation to different parts or aspects of the order. One such navigational tool is order queue 552. Order queue 552 may indicate an item location (e.g., tooth 422) that is currently being specified, within the context (e.g., mouth). The order queue 552 and/or tooth selector graphic 550 may change in appearance as the context, presented as the location in the mouth in this embodiment, of the item changes. For example, the tooth for which specifications are currently being made may be indicated by highlighting or other indication in order queue 552. Further, the context graphics (e.g., tooth selector graphic 550, order graphic 518, and/or order queue 552) may change with changes in the use installment.

If a user wishes to specify a different portion of the order (e.g., a different prescription within the same order such as an order for a different tooth), the order queue 552 may be configured such that it can be scrolled through to display several graphics, each graphic linked to order specifications for a corresponding tooth, for quick and efficient selectability of the sub-portions of the order. For example, if a user is generating an order for three teeth of a patient, the user may scroll to and select a first graphic whereby a screen associated with the order specifications for a first tooth is presented, and so on for the other teeth. That is, a user may point and select a second tooth for order, via the order queue 552. The order queue 552 may also be configured to graphically reflect a status of several parts of an order.

Figure 6:
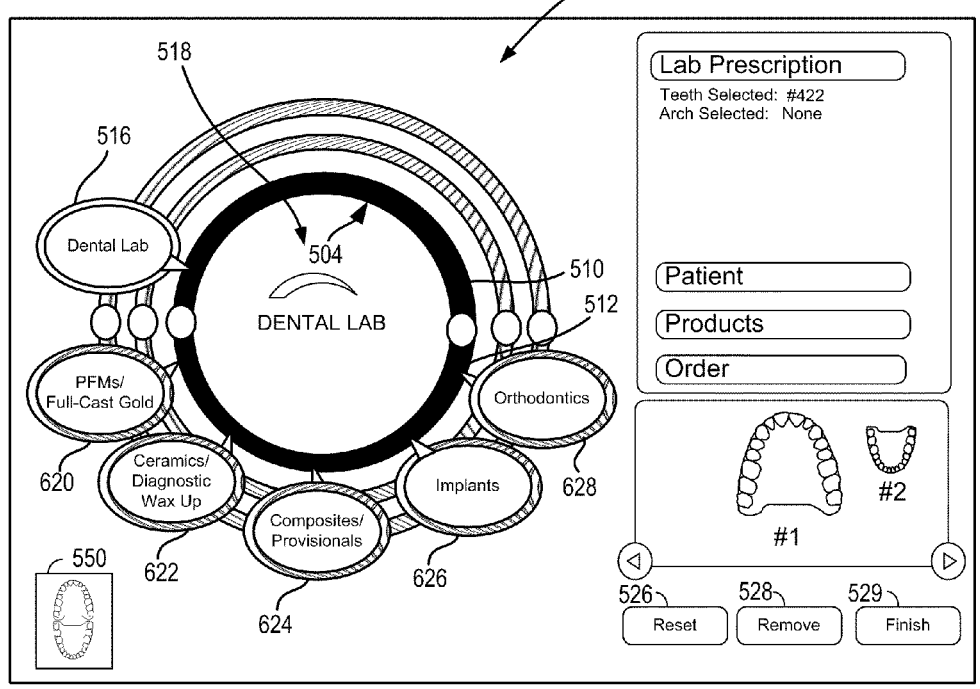
FIG. 6 illustrates a schematic view of another screen of the first embodiment of the graphical user interface of FIG. 4.
Figure 7:
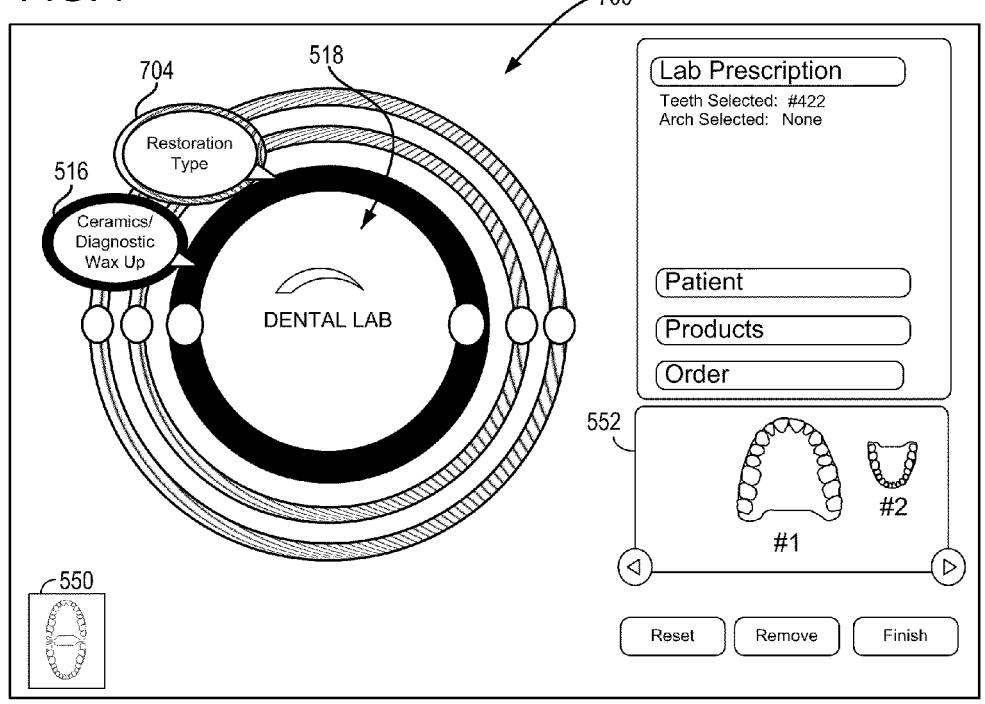
FIG. 7 illustrates a schematic view of another screen of the first embodiment of the graphical user interface of FIG. 4.

Selection of category indicator 516 of graphical order generator 502 may result in the displaying of screen 600 of FIG. 6. Referring now to FIG. 6, the order input tool 504 includes a category section 510 and an option section 512. The category section 510, presented as the upper portion of the innermost ring, is configured to display category indicators (e.g., category indicator) 516 selectable by the user to cause the option section 512, presented as the lower portion of the innermost ring, to display one or more option indicators for the selected category indicator. In this example, there are five selectable option indicators (e.g., 620, 622, 624, 626, and 628) associated with category indicator 516. Here, the plurality of category indicators and selectable option indicators are at least partially overlaid on the geometric pattern of the graphical order generator.

Category indicators are configured to include a graphical representation of a state of each category indicator. The state of each category indicator may include an active state, complete state, or incomplete state. The active state is a state in which an option indicator for that category indicator may be selected, the incomplete state is a state in which an option indicator for that category indicator has not yet been selected, and the complete state indicates a state in which a category option for that category indicator has been selected.

In FIG. 5, category indicator 516 is in an incomplete state, represented by a cross-hatched border of category indicator 516. This indicates category indicator 516 is not in the active state (e.g., has not yet been selected to be active) and also that an option indicator for the category indicator 516 has not yet been selected. Upon selection of category indicator 516, the category indicator is in an active state represented by a solid border for category indicator 516, as shown in FIG. 6. Once an option indicator is selected for category indicator 516, the category indicator 516 is in a complete state, represented by a dark border as shown in screen 700 of FIG. 7. As another example, a state of a category indicator may be reflected by category indicator color. For example, a category indicator in the active state may appear green, a category indicator in the complete state may appear red, and a category indicator in the incomplete state may appear grey.

Additionally, category titles may appear on category indicators in the active state and category indicators in the incomplete state to provide information about an active category indicator or an incomplete category indicator, respectively (see category indicator title "Dental Lab" on category indicator 516 in FIG. 5 and FIG. 6). On the other hand, a selected option indicator title may appear on category indicators in the complete state in order to provide visual feedback to a user regarding the selected option indicator for the respective category indicator (see option indicator title "Ceramics/Diagnostic Wax up" on category indicator 516 in FIG. 7).

Referring now to FIG. 6, when a category indicator is in the active state (e.g., category indicator 516 of FIG. 6), the option indicators 620, 622, 624, 626, and 628 associated with category indicator 516 are displayed for selection by the user. Here, order graphic 518 may be updated based on a user input device position (e.g., cursor position) hovering over a particular option indicator. For example, if a mouse is hovering on option indicator 620, a PFM graphic may be displayed as order graphic 518. In another example, the order graphic 518 may be updated based on time intervals, such that each of the graphics associated with each of the option indicators is displayed for a time interval before changing to a next graphic (e.g., graphics are cycled through). In this way, the order graphic 518 can assist a user in making decisions regarding the order. The order graphic 518 may be viewed in a two or three dimensional form from multiple perspectives, rotatable by the user, and may be updated on each screen of the GUI to visually model the item as option indicators are selected and/or as the order is refined.

When an option indicator for a category indicator is selected via user input, the category indicator changes from the active state to the complete state and the associated electronic dataset is updated by the selection of the option indicator for the respective category indicator. For example, when the option indicator 622 associated with the category indicator 516 is selected, a screen change to screen 700 of FIG. 7 occurs and category indicator 516 changes from the active state to the complete state. Although not shown at screen 700, order graphic 518 may also be updated to reflect the selection of option indicator 622.

The selection of an option indicator for a particular category indicator results in additional category indicators being displayed. That is, category indicators are progressively displayed throughout the order specification process, such that when a category indicator changes to the complete state, new category indicators which depend on or from the selected option indicators, are determined and automatically displayed. For example, upon selection of option indicator 622 for category indicator 516, category indicator 704 (which is dependent from option indicator 622) is determined and automatically displayed. However, in other examples, a subsequent category indicator may be independent of a previously-selected option indicator.

Further still, the number of category indicators in the incomplete state, and the category title of the category indicators in the incomplete state and the active state, can change as one or more category indicators change to the complete state. This is demonstrated by way of example as the number of category indicators changes from 1 to 2 when the screen changes from FIG. 6 to FIG. 7. Category indicator 704 is in an incomplete state in screen 700. Selection of category indicator 704 by user input, for example, may result in a screen change to screen 800 of FIG. 8. In other examples, election of option indicator 622 at screen 600 may result in the display of screen 800 of FIG. 8, thus skipping the display of screen 700.

Figure 8:
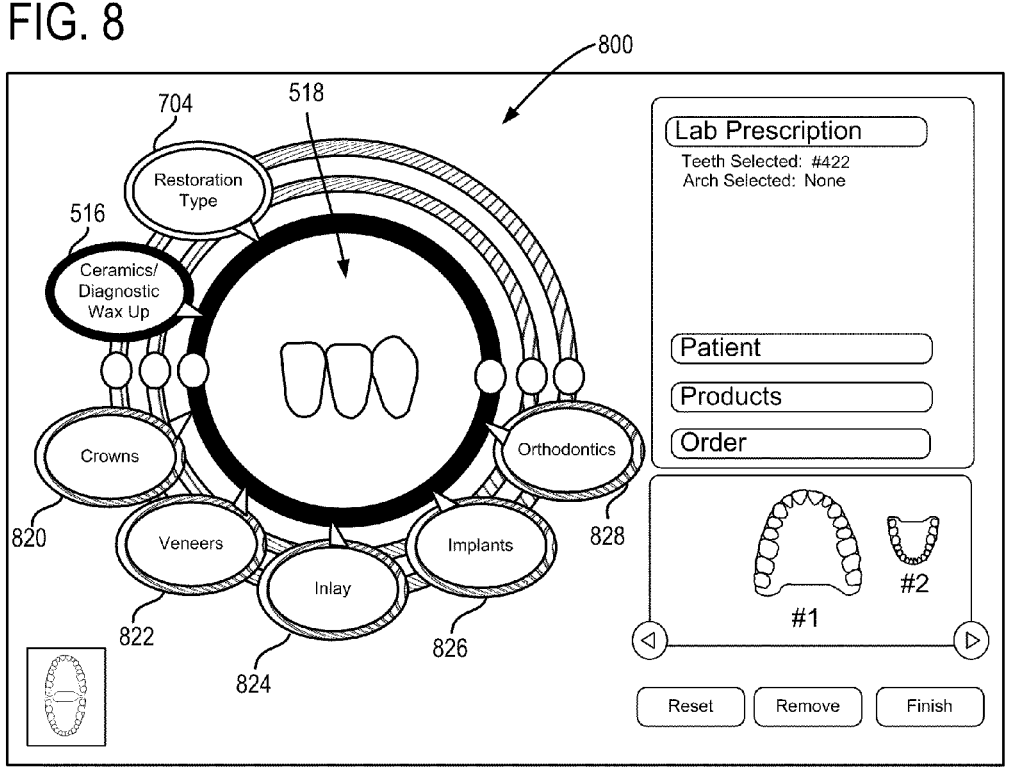
FIG. 8 illustrates a schematic view of another screen of the first embodiment of the graphical user interface of FIG. 4.
Figure 9:
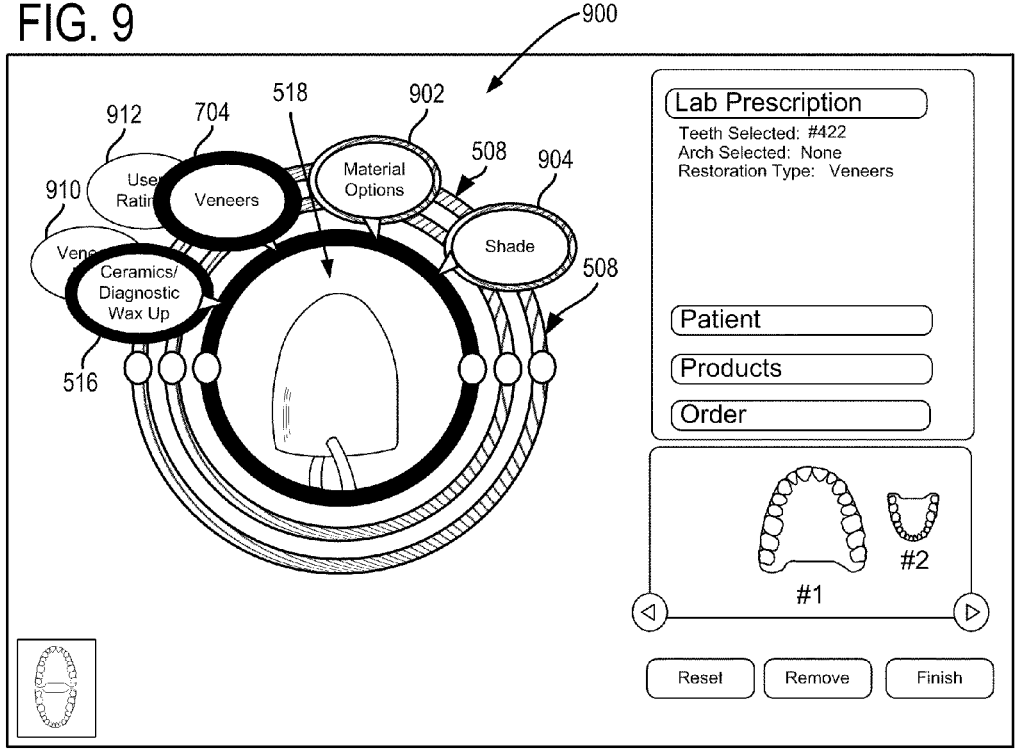
FIG. 9 illustrates a schematic view of another screen of the first embodiment of the graphical user interface of FIG. 4.

Referring now to FIG. 8, order graphic 518 has been updated to reflect selection of option indicator 622. Category indicator 516 is in the complete state, and category indicator 704 is in the active state. As such, option indicators 820, 822, 824, 826, and 828 are automatically displayed as they are associated with the category indicator 704. Here, selection of option indicator 822 by user input causes screen 900 of FIG. 9 to be presented. Order graphic 518 is updated to reflect selection of option indicator 822. Category indicator 704 is updated to include option indicator title "Veneers", and category indicators 902 and 904 are automatically displayed. Further, the dataset summary pane 520 is updated to read "Restoration Type: Veneers", thereby reflecting category indicator 704 in the complete state and the associated selected option indicator (e.g., "Veneers"). By automatically displaying category indicators 902 and 904, the graphical user interface reduces a chance that a user will forget to specify a material option and/or shade, and thus reduces a chance that a user will place an incomplete order.

Furthermore, selection of option indicator 822 from screen 800 results in an update of information indicators on contextual information tool 508 at screen 900. Information indicators 910 and 912 may be shown on screen 900, and may be visually linked to contextual information tool 508. In this example, the information indicators are shown in a background.

Figure 10:
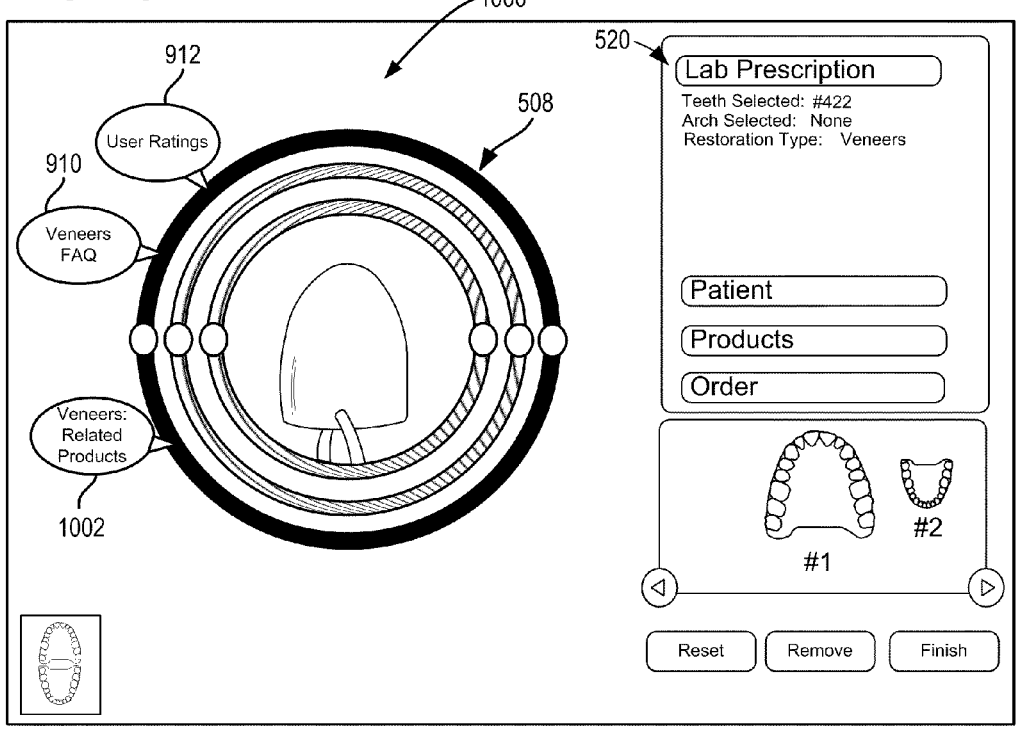
FIG. 10 illustrates a schematic view of another screen of the first embodiment of the graphical user interface of FIG. 4.

Selection of the contextual information tool 508 by user input may cause screen 1000 of FIG. 10 to be presented. The selection of the contextual information tool 508 may be indicated by a change in color of the ring representing the contextual information tool 508 (e.g., when contextual information tool 508 is given user focus). Here, the information indicators 910, 912, and 1002 are displayed in a foreground and category indicators 516, 704, 902, 904 may be shown in a background or may not be displayed.

In one example, a first portion (e.g., an upper half) of the contextual information tool 508 may include information indicators providing links to presentations, documents, websites, and other types of multimedia information. For example, information indicators 910, 912 may be presented in the upper half of contextual information tool 508, providing hyperlinks to websites or information services containing information on a recently selected option indicator, such as option indicator 822. In other examples, the information indicators may provide information relevant to the available option indicators for an active category indicator.

Upon selection of an information indicator, a link to one or more information services may occur. Alternatively or additionally, upon selection of an information indicator, an information sub-application may be executed or launched, and an associated information sub-application screen may be displayed. For example, selection of information indicator 912 may launch a mini-display of a website including user ratings for a variety of veneers. In other embodiments, selection of an information indicator may initiate display of information in a display area on the screen, such as in a portion of data summary pane 520. This is shown by way of example in FIGS. 17 and 18, discussed later.

Further, a second portion of a contextual information tool may include information indicators which, upon selection, link to information services, such as information sub-applications regarding products that complement the order (e.g., sponsor-based), products recommended by other users, products in stock by a vendor, etc.

Figure 11:
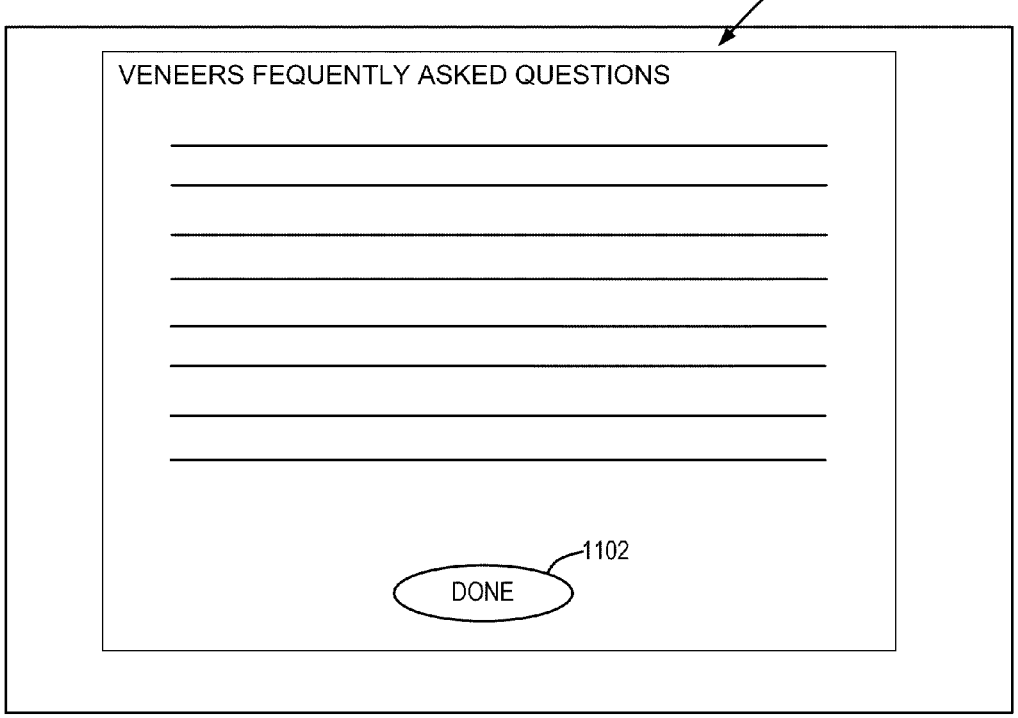
FIG. 11 illustrates a schematic view of another screen of the first embodiment of the graphical user interface of FIG. 4, the screen being associated with an information service.

At screen 1000, user input indicating a selection of information indicator 910 (e.g., "Veneers FAQ") results in drop-down screen 1100 of FIG. 11 being displayed. At FIG. 11, a drop-down screen 1100 is presented as overlaid upon screen 1000. Drop-down screen 1100 may be a screen associated with an information service (e.g., a PDF viewer, etc.) for displaying a text file. When a user is finished with screen 1100, selection of a "done" button 1102 may be received.

Information services may include a file including text or graphical information. In another example, an information service may include an information sub-application, such that when a corresponding information indicator is selected, the information sub-application is launched, or executed. An information sub-application may be interactive, by which a user may be provided information and/or from which the user can make a selection to further specify an order. Information services or information sub-applications may include objective information, ratings, and/or advertisements, as just some examples.

Information services, including information sub-applications, can be provided by the application running the graphical order generator GUI, or they may be provided by a third party. That is, information services and sub-applications may be external and/or internal to the application displaying the graphical user interface. External sources may include a third party data server, a remote data store or peer data store whereas an internal source may include a local data store. Information services which are internal may include media (e.g., pictures, videos, text documents, etc.) and instructions for displaying the media responsive to selection of a particular information indicator, which are included in an application or have been uploaded to the application. In some examples, files or sub-applications may be uploaded to an application running the graphical order generator so that upon selection of a particular category indicator, option indicator, communication indicator, or information indicator, a file may be displayed or a sub-application may be launched by the application. That is, the application may have capability for receiving information from external sources, whereafter the service or sub-application is considered to be internally sourced.

From the above discussion, it can be understood that information indicators may dynamically change to provide links to different sources as the state of the category indicators change and as option indicators change based on user input. Furthermore, the information indicators may dynamically change to link to different information services and/or may launch different information sub-applications as the state of category indicators and option indicators change.

Figure 12:
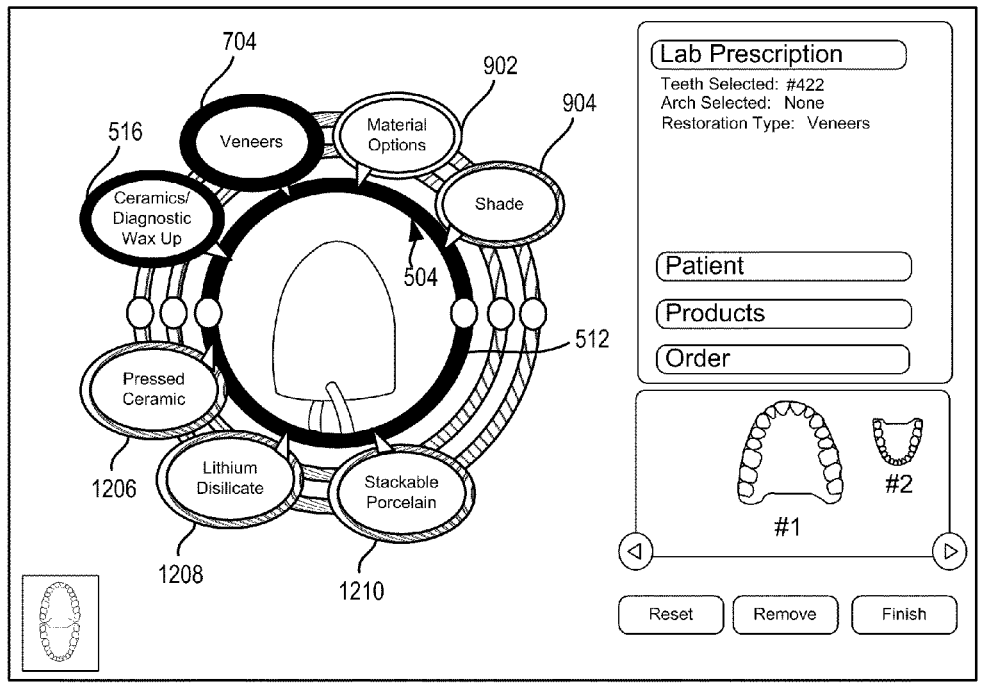
FIG. 12 illustrates a schematic view of another screen of the first embodiment of the graphical user interface of FIG. 4.

Referring now to FIG. 12, category indicator 902 has been selected and is thus in an active state. Category indicator 904 is in an incomplete state. Thus, in order to fully specify the item order, option indicators for at least category indicator 902 and category indicator 904 still need to be selected at this screen. In response to selection of category indicator 902, option indicators 1206, 1208, and 1210 are displayed in the option section 512 of the order input tool 504.

Figure 13:
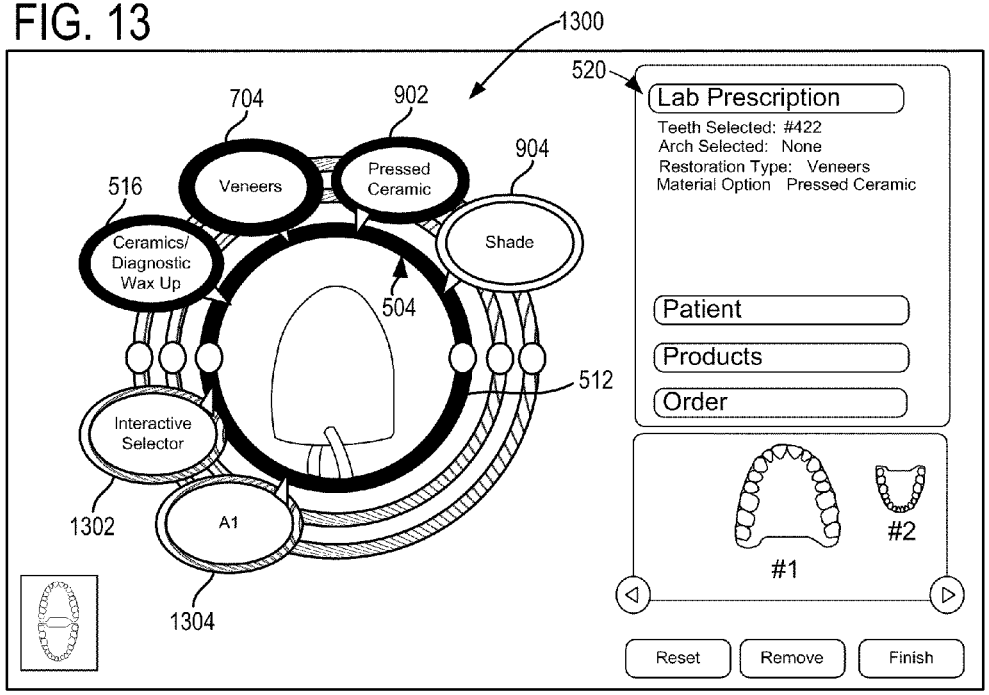
FIG. 13 illustrates a schematic view of another screen of the first embodiment of the graphical user interface of FIG. 4.
Figure 14:
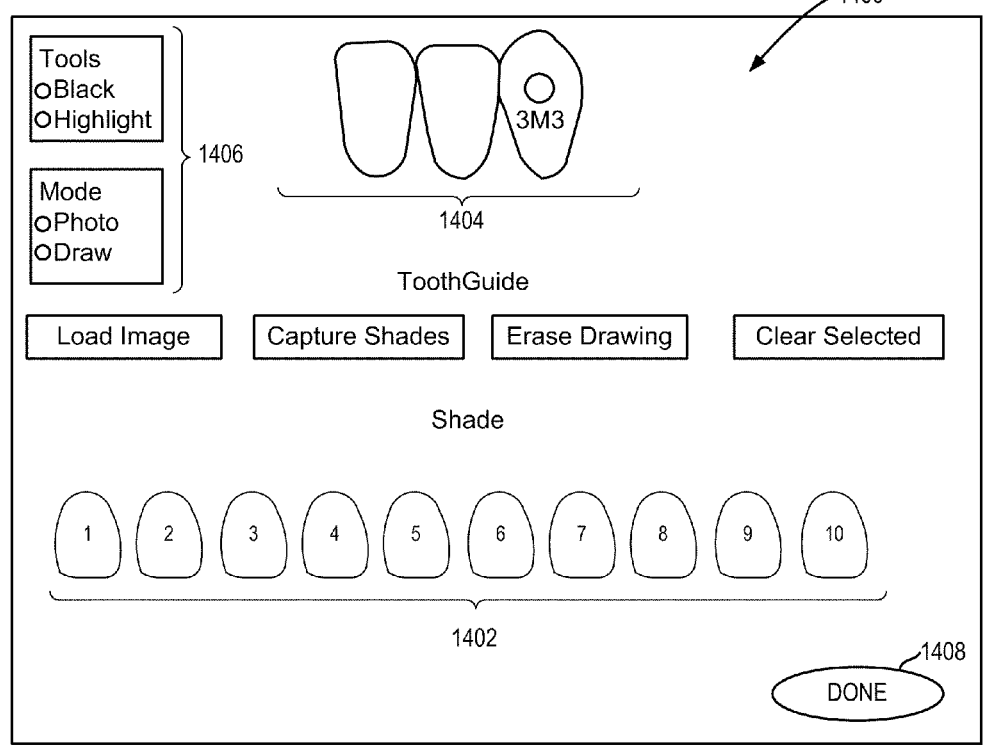
FIG. 14 illustrates a schematic view of another screen of the first embodiment of the graphical user interface of FIG. 4, the screen being associated with an option sub-application.

In response to selection of option indicator 1206 for category indicator 902, screen 1300 of FIG. 13 is presented on the display. Here, dataset summary pane 520 is updated to read "Material Option: Pressed Ceramic" to reflect the corresponding update to the electronic dataset. Screen 1300 of FIG. 13 illustrates category indicator 902 in a complete state, and category indicator 904 in an active state. Option indicators 1302 and 1304 are presented on the option section 512 of the order input tool 504. In response to selection of option indicator 1302, an option sub-application screen 1400 associated with an option sub-application is displayed, as shown at FIG. 14.

Option sub-applications may be similar to information sub-applications. That is, selection of an option indicator may result in execution of an option sub-application whereby a user can be provided with a plurality of sub-option indicators associated with various sub-options of an option indicator, in a similar manner as selection of an information indicator results in execution of an information sub-application. With respect to FIG. 14, an option sub-application screen 1400 is overlaid on screen 1300. In this specific example, the option sub-application screen 1400 provides a user with a vast amount of choices, and combinations of choices for specifying a shade of a tooth color for category indicator 904. That is, each shade (e.g., "3M3", "3L1.5", etc.) may be a sub-option indicator. Option sub-application screens may be particularly useful when a number of choices for specifying an option for the electronic dataset is large, or when the specification is complex. With the option sub-application screen 1400, one or more shades 1402 can be selected for application to at least a portion of one or more teeth. Furthermore, tools 1406 allow a user to annotate or draw particular characteristics of a tooth. As just some examples, tools 1406 may include highlighting for indicating decay, fluorousis, etc on particular portions of teeth. Further, tools 1406 may include photographic tools and drawing tools, whereby a user can upload photographs and/or make drawings to indicate specific sub-options. Thus, it can be understood that annotation by user input may be received by way of the option sub-application screen 1400.

As with information sub-applications, the option sub-application may be provided by an external or internal source. Further, a third party may upload an option sub-application to be integrated with the application displaying the order generator tool. The third party may also provide instructions for executing the option sub-application upon selection of a particular option indicator by a user. In this case, a third party may have specified, upon upload of the option sub-application, that the option sub-application screen 1400 should be displayed in response to selection of option indicator 1302. Thus, the option sub-application may be integrated with and executed by the application running the graphical order generator and thus may be executed on a same computing device. In another example, an option sub-application may be executed on a second computing device (e.g., over a computer network such as the Internet), and displayed on a same display that is presenting the graphical order generator. In other words, the option sub-application may be externally sourced. In this way, third party software providers can provide option sub-applications that interface with the graphical order generator.

An option sub-application may be executed, and a corresponding screen may be displayed on a display that is already displaying the graphical order generator. The option sub-application as shown in FIG. 14 includes a drop down screen, but it may be appreciated that an option sub-application screen can be any suitable screen format, such as an overlay on the GUI including the graphical order generator or a pop-up window. A user may be able to switch focus between the GUI associated with the graphical order generator and the option sub-application screen (or other linked media), for example by clicking on different portions of the display. In another example, the option sub-application screen may be integrated into the GUI associated with the graphical order generator. In another example, the user may be able to terminate the option sub-application (or other linked media) by selecting a close option such as close button 1408 on the option sub-application screen 1400. In response to receiving selection of the close button 1408, a previously-displayed screen may be displayed (e.g., screen 1300), or a new screen reflecting selection(s) made via interaction with the option sub-application screen 1400 may be displayed.

Figure 15:
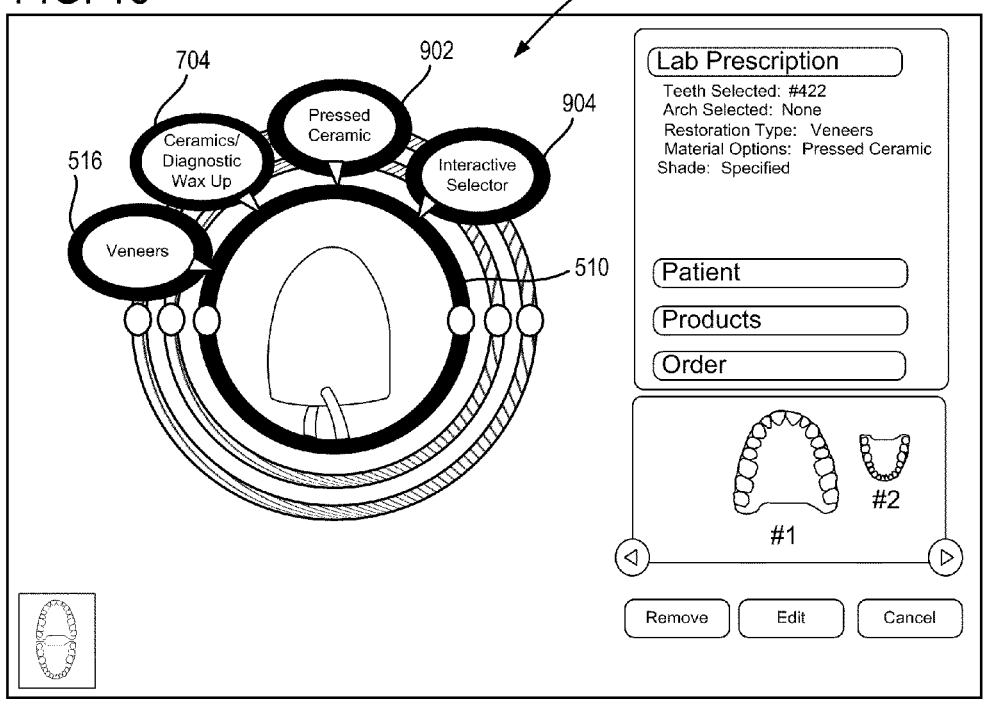
FIG. 15 illustrates a schematic view of another screen of the first embodiment of the graphical user interface of FIG. 4.

As shown in FIG. 15, category indicator 904 reflects selection of the option indicator 1302 by the graphical representation (e.g., dark border) of the complete state and by the option indicator title "Interactive Selector" displayed on category indicator 904. Additionally, completion of category indicator 904 is also reflected in dataset summary pane 520.

If category indicator 904 is now selected at screen 1500, such that category indicator 904 assumes an active state, option sub-application screen 1400 may again be displayed. Specifically, the option sub-application screen 1400, including the user selections and/or annotations and drawings, may be displayed and may be again modifiable.

Similarly, any of category indicators 516, 704, 902, and 904 in the complete state may be selected for modification from any of screens 900, 1200, 1300, or 1500, for example. In general, upon selection of a category indicator that is in the complete state, the category indicator may include a graphical representation of the category indicator in an active state, and corresponding option indicators may be displayed in the option section of the graphical order generator. Upon selection of a new or different option indicator for a first category indicator, the remaining category indicators may be updated, the electronic dataset may be updated, and the dataset summary pane 520 may also be updated. For example, one or more remaining category indicators may be removed if modification to the first category indicator deems the one or more remaining category indicators irrelevant (e.g., if a dental guard is selected, a color shade may not be relevant). In another example, one or more remaining category indicators may be updated to be in an incomplete state if the modification to the first category indicator requires or suggests a modification to the one or more remaining category indicators. However, in some cases, a first category indicator may be modified and the remaining category indicators may remain in the complete state, if the modification to the first category indicator is not inconsistent with option selections for the other category indicators.

In this embodiment, the category indicators 516, 704, 902, and 904 have an order in a hierarchy, and the order is rearrangeable by a user (e.g., by clicking and dragging category indicators on the screen via a data input device). This hierarchy is reflected by a hierarchy in the electronic dataset, as well as in a layout of the GUI. For example, at screen 1500 of FIG. 15, the hierarchy begins at the left of the category section 510 at category indicator 516 and moves downward to the right such that the bottom of the hierarchy is category indicator 904. To further stress the point, as shown in FIG. 15, category indicator 902 is below category indicator 704 in the hierarchy.

Referring now to screen 1600 of FIG. 16, category indicator 904 has been moved up the hierarchy via user input (e.g., clicking and dragging), to be above the category indicator 902 in the hierarchy. Category indicator 904 includes a graphical representation of the complete state, and category indicator 902 includes a graphical representation of the active state. Option indicators 1206 and 1208, associated with category indicator 902, are displayed. Notably, the option indicators on screen 1200 are different from the option indicators of screen 1600 even though a same category indicator is in the active state. Option indicator 1210 has been eliminated from the population of option indicators in screen 1600, by the moving of category indicator 904 above category indicator 902. Apparently, the moving of category indicator 904 has caused option indicator 1210 to be irrelevant. In other words, selection of a category indicator may filter subsequent category indicators, and selection of an option indicator may filter subsequent category indicators and/or option indicators. The dataset summary pane 520 is also updated to reflect the change to the electronic dataset.

When the order has been sufficiently specified by the user, meaning that option indicators for each category indicator have been selected, the order input tool 504, or graphical order generator 502, may visually indicate completion by each displayed category indicator including the graphical representation of the complete state. This is shown by way of example, in screen 1500 of FIG. 15. For example, completion of an order may include a change in color of all category indicators to red and each category indicator may display the selected option indicator title in text. Further, the electronic dataset associated with the category indicators in the complete state and the selected option indicators may be used to update the dataset summary text in the dataset summary pane 520 and to update the order graphic 518 such that it appears as a model of the ordered product or service. The electronic dataset can be output to a vendor computing device by the user via input at the control bar 524 (e.g., actuation of "finish" button 529).

Selection of the finish button 529 in the control bar 524 may generate an order identification, such as order identification 150. For example, a barcode may be generated as the order identification and transferred to a user via a peer-to-peer file transfer system. Thus, the user may print a label including the barcode, scan the barcode, and place the label on a physical package that is mailed to a laboratory. In one example, a dentist may make impressions of a patient mouth, for which the dentist ordered a crown. The dentist may then print out the barcode label, scan the barcode such that an application receives a signal that this item is being mailed, apply the barcode label to a package containing the impressions, and send it to a laboratory that will make the crown. The laboratory staff may receive the physical package and scan the barcode label. Thus, the application may receive a signal that the laboratory has received the item. The laboratory may then process the order (e.g., manufacture the crown) and mail the physical order with a physical label containing the same barcode. Digital output of processing (e.g., order details, mailing status, billing invoice, etc.) by the client and the laboratory, in this example, may be sent to an inbound message portion of the graphical order generator 502. It may be appreciated that an order identification such as a barcode, may be included on preprinted labels and/or printed programmatically.

The application disclosed herein may include a translation tool. For example, the dataset summary pane 520 including the text summary of the electronic dataset may be presented in different languages. Further, the user may select a language in which to display text. Each category and option indicator may have pre-assigned phrases in a foreign language to allow for consistency of language translation.

Throughout the order specification process, the communication tool 506, represented by the middle ring of the graphical order generator 502 is configured to display current and previous communication indicators corresponding to current or past communication messages. Communication indicators may include annotations by a user and/or communications to and from other users, wherein communication data is sent and received via a peer-to-peer protocol. For example, a user may provide, to a vendor, a text message specifying a parameter of the item. As additional examples, a user may provide (e.g., upload) an image, an audio communication, and/or a video communication to the application, and the communication may be represented by a communication indicator. Upon selection of a communication indicator, the image, audio communication and/or video communication may be presented or played. Where a media file is provided with an item order, a media icon may appear in the dataset summary pane 520. Further still, the communication messages may include annotations by a user of the graphical user interface.

In one example, one portion of communication tool 506 may include inbound messages and another portion may include outbound messages. For example, an upper portion of the communication tool 506 may include inbound messages including order status updates from the laboratory (e.g., date and time the mouth impressions for a crown are received, date and time an order is being processed for a user) and billing invoices, as some examples. Further, a lower portion of the communication tool 506 may include outbound messages including order placement and order status inquiries (e.g., dentist may inquire regarding costs), as some examples. In one example, the messages may be arranged in chronological order and persist such that each time a user accesses a particular item order, all messages in the history of the item order may be presented at the communication tool. However, communication messages may be arranged and/or sorted in any desirable manner (e.g., chronologically, based on recipient, based on conversation, etc.).

An alternate embodiment of the graphical order generator 502 is described with respect to FIG. 17 and FIG. 18. Specifically, a different layout of the contextual information tool 508 of graphical order generator 502 is discussed. At screen 1700 of FIG. 17, a user may be ordering a crown in a dental context and a portion of the contextual information tool 508 may populate with related product links to products that complement a crown restoration (e.g., cements, finishing/polishing, impression materials). Here, a bottom half of the contextual information tool 508 includes related product links 1702, 1704, 1706 which, upon selection, may present more detailed information regarding the products associated with the selected related product link. Further, the order information window 522 may include a related products pane 1710. The related products pane 1710 may include descriptions for each of the products associated with the related product links 1702, 1704, and 1706, or this information may be displayed as embedded information in an alternative display area associated with the contextual information tool 508. In some examples, the information is from third party sources.

Related product link 1702 associated with cements may be selected, thus causing the screen 1800 of FIG. 18 to be presented. In FIG. 18, a selectable back link 1802 is presented to allow the user to navigate to the previous screen 1700. Product detail links 1812 and 1814 regarding two types of available cement are also presented, at the contextual information tool 508, for selection. If product detail link 1812 associated with a first type of cement is selected, a text description of the product associated with product detail link 812 may be presented in the related products pane 532. Further, more options may be presented in the related products pane, such as a description of a second cement (e.g., associated with information indicator 1814). Additional options that may be displayed include related product information, related product instructions, related product communication request, link to discussion forums, add product to a favorites list, product rating, user history, and an option to order the product. Thus, it may be appreciated a user may further investigate cement, ask to speak to the representative of a dental cement company, may be able to post and respond to messages on a dental cement forum, add the first type of cement to a favorites list for future use, rate the dental cement, and assess personal history with this type of cement, as some examples.

The graphical order generator 502 described herein may be used for item or service ordering, treatment planning, entry of treatment notes to a medical record, billing, and/or diagnostics, as just some examples in a medical context. An additional embodiment of the graphical user interface in a dermatological use context is described with respect to FIG. 19 and FIG. 20. Specifically, the graphical user interface may be used by a doctor's office to enable a patient to complete intake information via the graphical user interface. Thereafter, the graphical user interface may be accessible by a plurality of healthcare providers.

Figure 19:
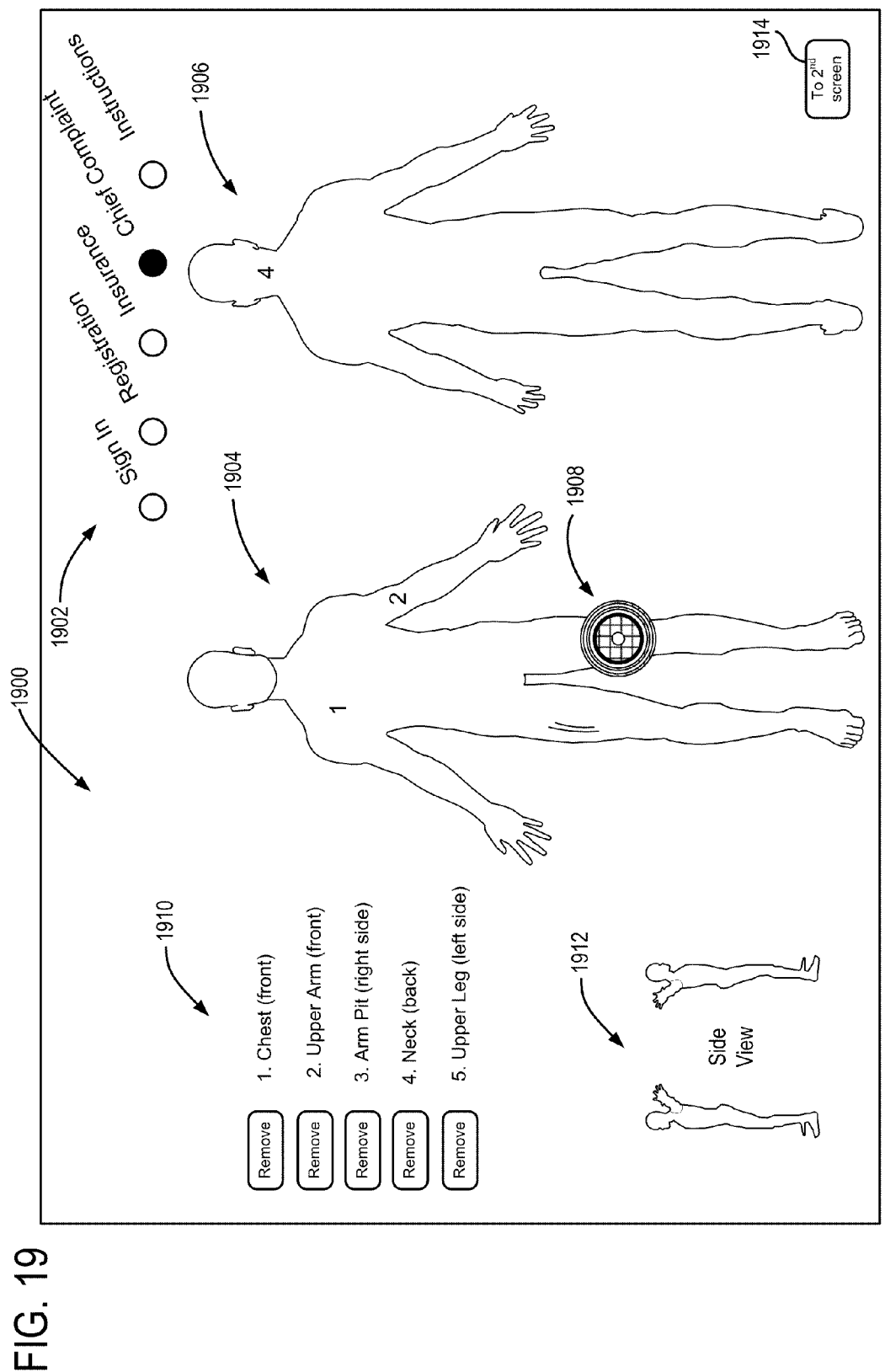
FIG. 19 illustrates a schematic view of a screen of a third embodiment of a graphical user interface for selecting an item for specification.

Referring now to FIG. 19, item selection screen 1900 is shown. A toolbar 1902 allows a user (e.g., a patient or doctor) to navigate between separate sections of the graphical user interface. At screen 1900, "Chief Complaint" in the toolbar 1902 is highlighted, indicating that a user is currently interacting with this section of the graphical user interface.

A cursor 1908 can be dragged around item selector graphic 1904 and/or item selector graphic 1906 to specify a body part for selection. When a user places, or hovers, the cursor 1908 over a body part, the user can then actuate the cursor 1908 to select the body part. In this example, the user has actuated the cursor 1908 over the upper leg (left side), and as such, this body part is added to a list of complaints 1910.

Additional item selector graphic 1912 can be selected at screen 1900, by user input. In response to selection of item selector graphic 1912, item selector graphic 1904 and/or item selector graphic 1906 may be replaced with an enlarged version of item selector graphic 1912. By providing several versions of an item selector graphic, a user may be able to more accurately specify where the item (e.g., body part) complaint is located, in this example.

As can be seen from the list of complaints 1910, a user has recorded five body parts. The list of complaints 1910 may include a user history from previous usage of the graphical user interface (e.g., a patient history from several visits), or the list of complaints 1910 may include only currently selected body parts, reflecting a current usage of the graphical user interface.

When a user has selected one or more body parts, the user can select navigation graphic 1914 to navigate to a second screen 2000 of the graphical user interface. In another example, the cursor 1908 may be dragged around item selector graphic 1904 and/or item selector graphic 1906, and upon selection of a body part, the screen 2000 including an order generator tool may be automatically displayed.

Figure 20:
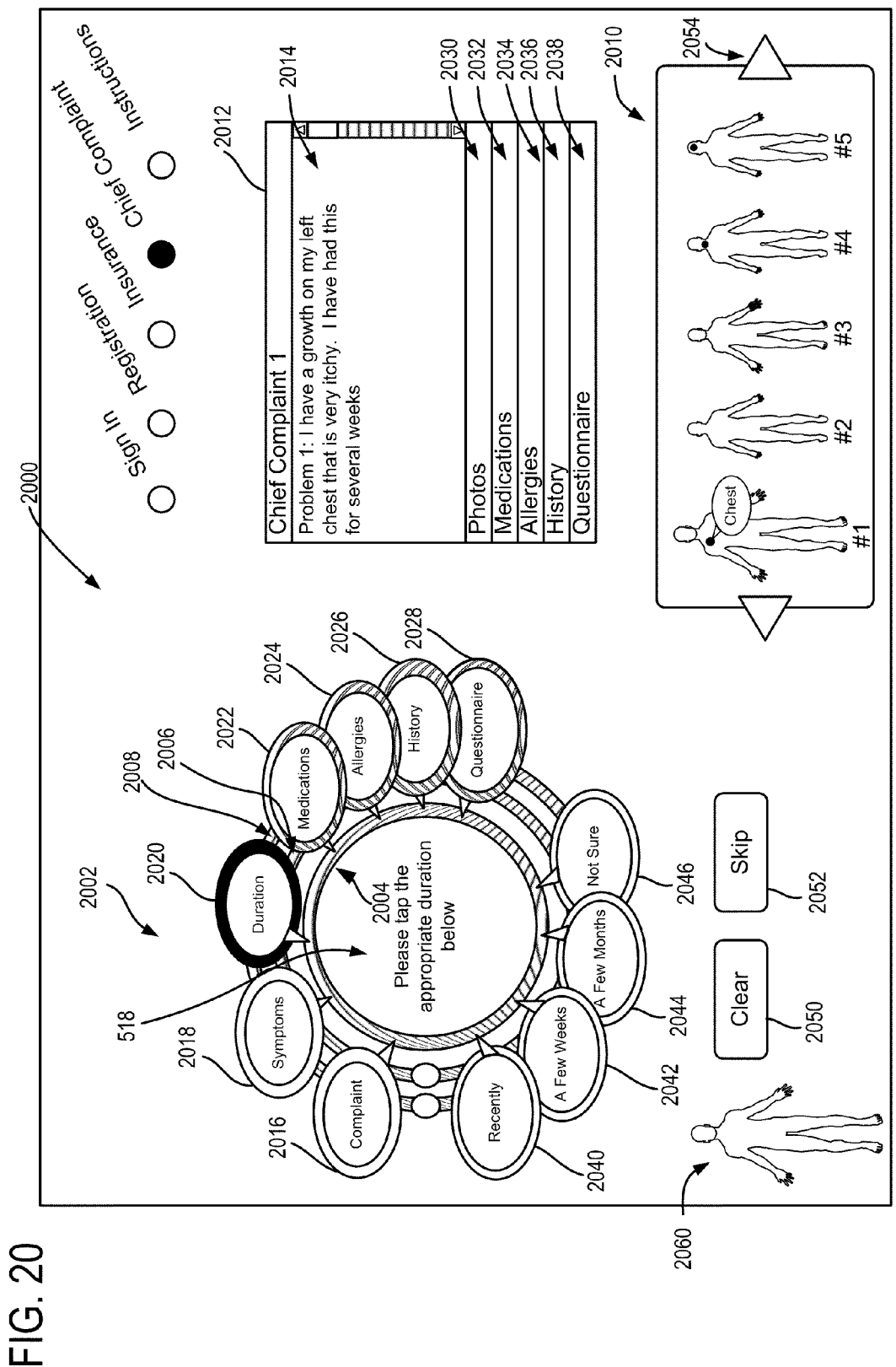
FIG. 20 illustrates a schematic view of another screen of the third embodiment of a graphical user interface of FIG. 19.

Turning now to FIG. 20, screen 2000 is displayed. Here, graphical order generator 2002 is displayed, having an order input tool 2004, a communication tool 2006, and a contextual information tool 2008. A plurality of category indicators are shown overlaid on the geometrical arrangement of graphical order generator 2002.

The current complaint (complaint #1) being specified is indicated by an enlarged or highlighted graphic in the order queue 2010. The current complaint being specified is also indicated by data window 2012 which displays a text summary of chief complaint #1 in a chief complaint description pane 2014.

Here, category indicator 2016 is in a complete state, and a user may have already entered at least a partial text description of the chief complaint for complaint #1, as indicated at chief complaint description pane 2014. A photo pane 2030 of data window 2012 is shown as collapsed, but may be expanded to enable a user to upload or view a photo related to a current chief complaint. Category indicator 2018 is also in a complete state, and category indicator 2020 is in an active state. Related to category indicator 2020, option indicators 2040, 2042, 2044 and 2046 are displayed as graphically overlaid on an option section of order input tool 2004. Selection of one of the option indicators by user input may result in an update to the electronic dataset associated with chief complaint #1 (e.g., body part complaint), as well as an update to the text summary displayed in the chief complaint description pane 2014.

Category indicators 2022, 2024, 2026, and 2028 are displayed in an incomplete state. Upon selection of category indicator 2022, a graphical representation of an active state may be displayed and data window 2012 may be updated to expand a medications pane 2032, where a text summary of previous, current, or prospectively prescribed medications may be displayed. Upon selection of category indicator 2024, a graphical representation of the active state may be displayed and data window 2012 may be updated to expand an allergies pane 2034 specifying a patient's allergies. Similarly, selection of category indicator 2026 may cause an expansion of history pane 2036, and selection of category indicator 2028 may cause an expansion of questionnaire pane 2038. The panes of data window 2012 may allow for text, graphical or other input and/or viewing, by a user.

Actuation of a clear button 2050 may result in clearing, or resetting, of one or more option indicator selections. Actuation of a skip button 2052 may enable a user to more enjoyably navigate the graphical order generator 2002 by selecting inputs in a user-defined order. Other buttons are conceivable for editing, printing, completing an order, etc.

A user can navigate to a second (or third, fourth, etc.) complaint from screen 2000, by actuation of navigation controls of order queue 2010. For example, actuation of a right arrow 2054 may result in display of a screen including a graphical order generator for specification of complaint #2. Item selection graphic 2060 may allow the user to navigate to item selection screen 1900.

The systems and methods described herein are not limited to medical implementations, but rather, are suitable for any type of item or service order, such as for ordering automobile items, home repair services, legal services, etc.

Various programming techniques may be used to implement the systems and methods described above. For example, a mark-up language such as XML may be used. In one example, an order generator script (OGS) may be established to define requirements, inputs and outputs, and workflow logic. An instance of each OGS may be attached to each order, and include information on the state of the order, to maintain order and version integrity. OGS also makes it possible to recall and reuse previous orders via the graphical user interface described above, without starting from scratch. For example, category indicators and option indicators may be visually stacked and un-stacked, for the purpose of grouping and/or aggregating common, and/or associated options and/or tasks. Additionally, this may enhance and optimize interaction and usability. Furthermore, a graphical order generator may be configured to accommodate both a production and reactive rule engine, in some examples.

The graphical order generator may be used in a multi-user workflow such that an electronic dataset associated with an order may be influenced by multiple individuals, in some examples. Further, the graphical order generator may be used for any order tracking, order collaboration, order oversight, quality control, inspection, etc. Thereby, it may be appreciated that usage patterns may be collected and analyzed from an order input tool to ultimately allow users of a graphical order generator to view a most common approach or an ideal approach for generating a particular order using the order input tool, in one example. Further, a most common approach or a most ideal approach may be compared to the user's approach, and automatically or semi-automatically modified according to a user's approach. That is, any user may be able to manage and/or modify a presentation or appearance of the graphical order generator using a graphical order generator building tool. Such a building tool may allow a third party to upload media and/or sub-applications, as mentioned above. The building tool may also allow a third party to instruct when and/or how the media and/or sub-applications are to be displayed within the graphical order generator.

Further still, commonly viewed, commonly selected, or popular category indicators may be displayed first, or prominently. Similarly, commonly selected or popular option indicators within a category indicator may be displayed first or prominently. In this way, the graphical order generator may be a "smart" or adaptive tool.

The graphical order generator can be modified for existing businesses, such as vendors of other products and services. That is, an existing knowledge base can be integrated into a graphical order generator for clinical usage, prescription placement, treatment planning, diagnostics, annotation, charting, medical billing, research, censuses, continuing education, etc.

The graphical order generator can also make use of knowledge of an inventory of a vendor or of a client, such that the category indicators and option indicators provided with the graphical order generator are up-to-date and reflect a vendor's available inventory and/or a client's inventory. In this way, a client may quickly know what is available for order, and/or whether or not the client already has some components in the client's own inventory. Further, the graphical order generator may be configured to recommend items for order based on a knowledge of a client's inventory (e.g., via the contextual information tool). This may be referred to as just-in-time inventory.

In another example, the graphical order generator can be used to standardize aspects of a website into a single interface. For example, departments or sections of a business such as sales, marketing, communication, workflow, and support may be integrated into a single, intuitive interface using the graphical order generator.

It will be appreciated that the computing devices described herein are any suitable computing devices configured to execute the programs described herein. For example, the computing devices is a mainframe computer, personal computer, laptop computer, portable data assistant (PDA), computer-enabled wireless telephone, networked computing device, or other suitable computing device, and is connected to each other via computer networks, such as the Internet. These computing devices typically include a processor and associated volatile and non-volatile memory, and are configured to execute programs stored in non-volatile memory using portions of volatile memory and the processor. As used herein, the terms "application" and "sub-application" refers to software or firmware components that is executed by, or utilized by, one or more computing devices described herein, and is meant to encompass individual or groups of executable files, data files, libraries, drivers, scripts, database records, etc. It will be appreciated that computer-readable media is provided having program instructions stored thereon, which upon execution by a computing device, cause the computing device to execute the methods described above and cause operation of the systems described above.

It should be understood that the embodiments herein are illustrative and not restrictive, since the scope of the invention is defined by the appended claims rather than by the description preceding them, and all changes that fall within metes and bounds of the claims, or equivalence of such metes and bounds thereof are therefore intended to be embraced by the claims.

The invention claimed is:

1. A graphical user interface displayed on a display of a computing device, having a processor and a memory, for specifying characteristics of a custom-made medical or dental item comprising:
   an item selection screen configured to display a selectable medical or dental item;
   and
   a graphical order generator arranged in a geometric pattern, and displayable in response to selection of the selectable medical or dental item, including:
   an order input tool including:
   a category section configured to display a plurality of inter\-dependent dynamically filtered medical or dental category indicators arranged in a sequential and user-modifiable hierarchy, each medical or dental category indicator including a graphical representation of an active state, a complete state, or an incomplete state, and
   an option section configured to display a plurality of selectable medical or dental option indicators associated with a category indicator, where the medical or dental category indicator includes the graphical representation of the active state or incomplete state prior to selection of an option indicator, and the medical or dental category indicator includes the graphical representation of the complete state after selection of the option indicator,
   a communication tool configured to display a plurality of selectable communication indicators, the communication indicators associated with one or more past or current communication messages, and
   a contextual information tool configured to display one or more selectable information indicators, the information indicators dynamically updateable in response to a change of state of the medical or dental category indicator and in response to a change of selectable option indicators;
   wherein the geometric pattern of the graphical order generator includes a plurality of nested ring elements, the order input tool being in a form of a first ring element of the plurality of nested ring elements, the communication tool being in a form of a second ring element of the plurality of nested ring elements, and the contextual information tool being in a form of a third ring element of the plurality of ring elements;
   wherein the communication indicators of the communication tool are associated with a plurality of communication messages including annotations by a user of the graphical user interface and/or communication messages sent to and/or received from other users;
   wherein when an order is finished the graphical order generator is configured to generate an order identification~print a label of the order identification for mailing a specimen for the order to a laboratory and transfer an electronic copy of the order identification in an electronic dataset with other parameters of the order to the laboratory for processing; and
   wherein the graphical order generator includes an inbound message portion configured to receive digital output from the laboratory indicating a status of processing of the order at the laboratory.

2. The graphical user interface of claim 1, further comprising an order graphic which is updated to reflect selection of one or more of the medical or dental category indicators and selection of one or more of the option indicators.

3. The graphical user interface of claim 1, further comprising an option sub-application displayable in response to selection of the option indicator, wherein the option sub-application is configured to display one or more sub-option indicators associated with the option indicator, and to receive a selection of one or more of the sub-option indicators.

4. The graphical user interface of claim 3, wherein the option sub-application is further configured to receive annotation via user input.

5. The graphical user interface of claim 1, further comprising an order information window configured to display a text summary of the electronic dataset.

6. The graphical user interface of claim 1, wherein the plurality of communication messages are sent and received via a peer-to-peer protocol.

7. The graphical user interface of claim 1, where the information indicators each include a link to a respective information service, such that upon selection of an information indicator, an information service is displayed.

8. The graphical user interface of claim 7, where the information service is an information sub-application.

9. The graphical user interface of claim 8, where the information sub-application is supplied by a third party, and the information sub-application is integrated with an application running the graphical order generator.

10. A method for ordering a medical or dental item by specifying an electronic dataset, the method comprising:
displaying a graphical order generator arranged in a geometric pattern, the geometric pattern including a plurality of nested ring elements, the graphical order generator including an order input tool configured to display a plurality of inter\-dependent dynamically-filtered medical or dental category indicators arranged in a sequential and user-modifiable hierarchy, the order input tool being in a form of a first ring element of the plurality of nested ring elements, a communication tool being in a form of a second ring element of the plurality of nested ring elements, and an information tool configured to display one or more information indicators, the information tool being in a form of a third ring element of the plurality of ring elements, where a first one of the medical or dental category indicators is displayed with a graphical representation of an incomplete state;
in response to a selection of the first one of the medical or dental category indicators:
displaying a plurality of selectable option indicators associated with the first one of the medical or dental category indicators;
displaying the first one of the medical or dental category indicators with a graphical representation of an active state, and
updating the one or more information indicators based on the active state of the first one of the medical or dental category indicators and based on the plurality of selectable option indicators;
in response to a selection of one of the selectable option indicators:
updating the electronic dataset to include option data associated with the one of the selectable option indicators;
generating an order identification;
printing a label of the order identification for mailing a specimen for the order to a laboratory;
transferring an electronic copy of the order identification in the electronic dataset with other parameters of the order to the laboratory for processing;
receiving digital output from the laboratory indicating a status of processing of the order at the laboratory;
displaying the first one of the medical or dental category indicators with a graphical representation of a complete state; and
outputting the electronic dataset.

11. The method of claim 10, further comprising, in response to selection of the one of the selectable option indicators, displaying a second one of the category indicators with a graphical representation of an incomplete state, the second one of the category indicators being lower in the hierarchy than the first one of the medical or dental category indicators.

12. The method of claim 11, further comprising moving the second one of the medical or dental category indicators higher in the hierarchy than the first one of the medical or dental category indicators, responsive to user input.

13. The method of claim 12, further comprising updating the plurality of selectable option indicators associated with the first one of the medical or dental category indicators based on the moving of the second one of the medical or dental category indicators.

14. The method of claim 10, further comprising at least partially overlaying the plurality of medical or dental category indicators and the plurality of selectable option indicators on the geometric pattern of the graphical order generator.

15. The method of claim 10, further comprising displaying a plurality of communication indicators associated with one or more past or current communication messages in response to selection of the communication tool, where the electronic dataset includes communication data associated with the one or more past or current communication messages.

16. The method of claim 10, further comprising displaying an information service in response to selection of an information indicator, where the information service includes one or more of an informational file and an information sub-application.

17. The method of claim 10, further comprising displaying an item selection screen including a selectable item, and receiving a selection of the selectable item, where displaying of the graphical order generator occurs after receiving the selection of the selectable item.

18. A system for specifying a custom-made medical or dental order, the system comprising:
a computing device, having a processor and a memory, configured to execute an application for specifying an electronic dataset associated with the custom-made medical or dental order; and
a display associated with the computing device for displaying a graphical user interface including a graphical order generator arranged in a geometric pattern, the geometric pattern including a plurality of nested ring elements, the graphical order generator including:
an order input tool configured to display a plurality of inter-dependent dynamically filtered medical or dental category indicators arranged in a sequential and user-modifiable hierarchy, and further configured to display a plurality of selectable option indicators associated with a category indicator in response to selection of the medical or dental category indicator, the order input tool being in a form of a first ring element of the plurality of nested ring elements,
where prior to selection of an option indicator, the medical or dental category indicator includes a graphical representation of an active state or an incomplete state, and where in response to selection of the option indicator, the medical or dental category indicator includes a graphical representation of a complete state and the electronic dataset is updated to include an option associated with the option indicator, a communication tool configured to display a plurality of selectable communication indicators, the communication indicators each associated with one or more past or current communication messages, where the electronic dataset includes communication data associated with the one or more past or current communication messages, the communication tool being in a form of a second ring element of the plurality of nested ring elements; and a contextual information tool configured to display one or more selectable information indicators which are dynamically updateable based on one or more of the selection of the medical or dental category indicator and the selection of the option indicator, each information indicator including a link to an information service, the contextual information tool being in a form of a third ring element of the plurality of ring elements;

wherein the communication indicators of the communication tool are associated with a plurality of communication messages including annotations by a user of the graphical user interface and/or communication messages sent to and/or received from other users~ wherein when an order is finished the graphical order generator is configured to generate an order identification, print a label of the order identification for mailing a specimen for the order to a laboratory~and transfer an electronic copy of the order identification in the electronic dataset with other parameters of the order to the laboratory for processing; and wherein the graphical order generator includes an inbound message portion configured to receive digital output from the laboratory indicating a status of processing of the order at the laboratory.

19. The system of claim 18, where the computing device is further configured to output the electronic dataset upon completion of the custom-made order, and where the electronic dataset includes the order identification.

\* \* \* \* \*